(12) United States Patent
Sauter, Jr.

(10) Patent No.: US 9,120,107 B1
(45) Date of Patent: *Sep. 1, 2015

(54) ENHANCED IBF, HYBRID, N-CHANNEL, X-LOCAL, Y-ENERGY MODE, Z-COUPLED NESTED GAUSSIAN SURFACES FOR LIQUID(S) DISPENSING, LIQUID(S) TREATMENT, LIQUID(S) INTRODUCTION AND SOLID(S) PRODUCTION VIA INDUCTION BASED FLUDICS METHODS AND APPARATUS

(76) Inventor: Andrew Daniel Sauter, Jr., Henderson, NV (US)

( * ) Notice: Subject to any disclaimer, the term of this patent is extended or adjusted under 35 U.S.C. 154(b) by 549 days.

This patent is subject to a terminal disclaimer.

(21) Appl. No.: 12/803,678

(22) Filed: Jul. 2, 2010

Related U.S. Application Data

(63) Continuation-in-part of application No. 11/137,254, filed on May 25, 2005, now Pat. No. 7,749,447.

(51) Int. Cl.
| | | |
|---|---|---|
| *B05B 5/00* | (2006.01) | |
| *H01J 49/16* | (2006.01) | |
| *B05B 5/025* | (2006.01) | |
| *B05B 5/043* | (2006.01) | |
| *H01J 49/00* | (2006.01) | |

(52) U.S. Cl.
CPC . *B05B 5/001* (2013.01); *B05B 5/00* (2013.01); *B05B 5/0255* (2013.01); *B05B 5/043* (2013.01); *H01J 49/00* (2013.01); *H01J 49/165* (2013.01)

(58) Field of Classification Search
USPC ............................ 422/504; 210/656; 250/288
See application file for complete search history.

(56) References Cited

U.S. PATENT DOCUMENTS 7,189,977 B2 * 3/2007 Yamaguchi et al. .......... 250/425

OTHER PUBLICATIONS

Sauter et al., "Nanoliters onto media: Use of electric induction", Oct. 2001, American Laboratory, pp. 40-45.*

* cited by examiner

*Primary Examiner* — Jonathan Hurst

(57) ABSTRACT

Femtoliter to milliliter volumes of one or a plurality of different liquids are accurately transported, dispensed and/or treated where the fluids are energized purely electrokinetically or in a hybrid mode where auxiliary coordinated energy sources including but not limited to pneumatic, piezoelectric; peristaltic; ultrasonic; thermal; gravitational, acoustic are employed concurrently or sequentially to transport liquids for various purposes from diverse devices to targets of all types being made of a conductive, non-conductive or semiconductive materials. Liquids in nested Gaussian surfaces or common liquid handling devices (e.g., syringes, pipettes, pumps) or more complicated devices (Nanoscreen's syringes or Roche's polypipetter) can be energized by use of one source of energy and also by electric induction or conduction of lumen or targets or both and are optionally concurrently or sequentially combined with non electrical energy to effect highly accurate volumetric and spatial liquid transport with active or passive flight direction yielding non touch or touch liquid sample placement, parallel dispensing, with or without filtration, SPE, LC, or other treatment technologies and for scientific instrument introduction for IBF, MALD, DESI, DART and other sample introduction and for drug delivery, diagnostics, manufacturing of products, product tagging, sample preparation or related applications.

19 Claims, 57 Drawing Sheets

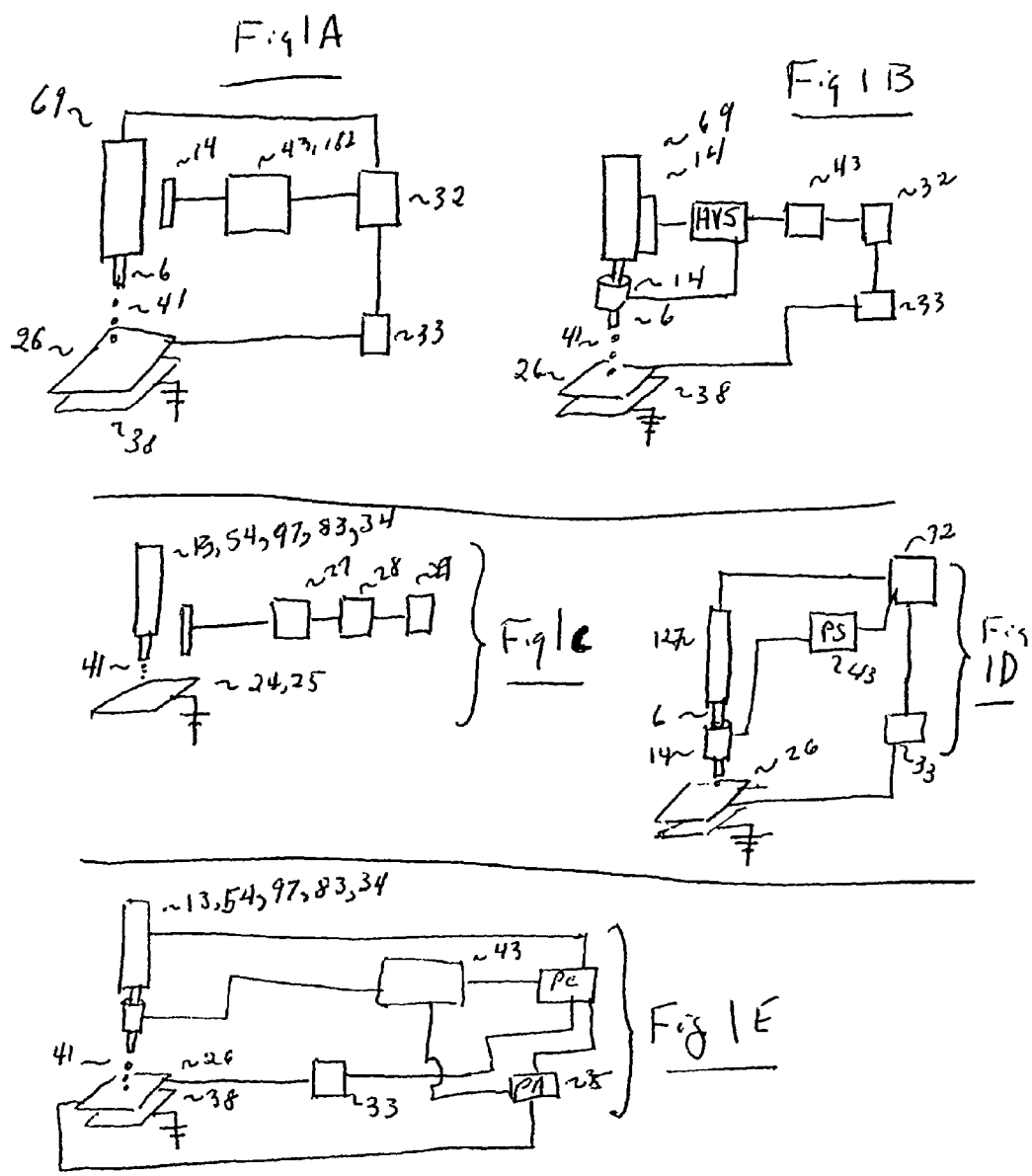
Figure 1. nL dispensing, treatment devices, & configurations

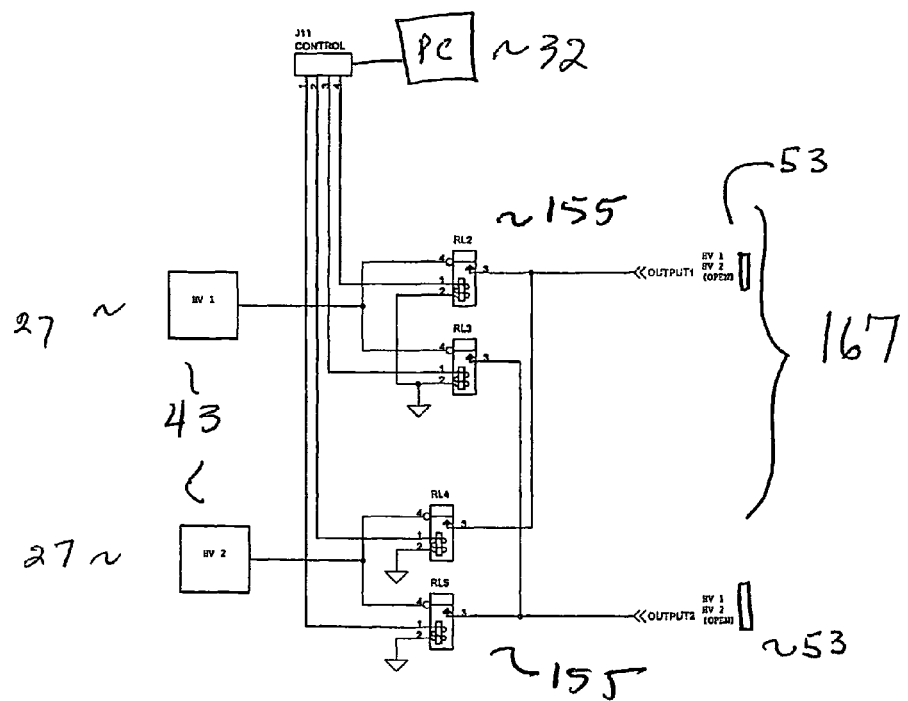
Figure 2 Bilocal, Bipolar Power Supply Fluidic Drive Circuit + Gaussians

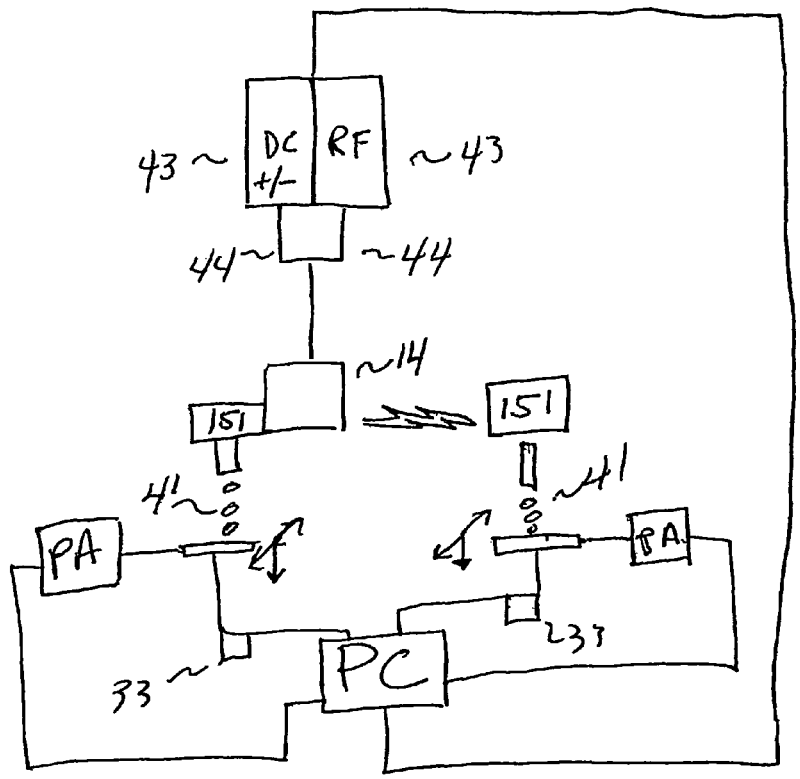
Figure S Version 2.0 of driving & counting circuit of the digital NANOLITER COCH WAVE.

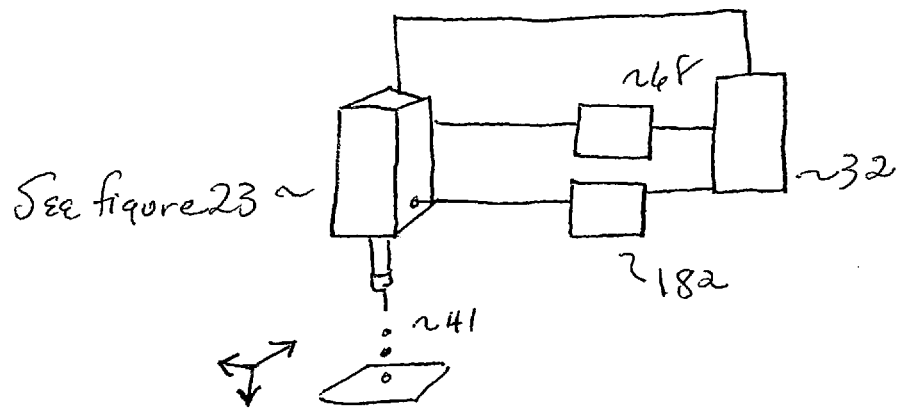
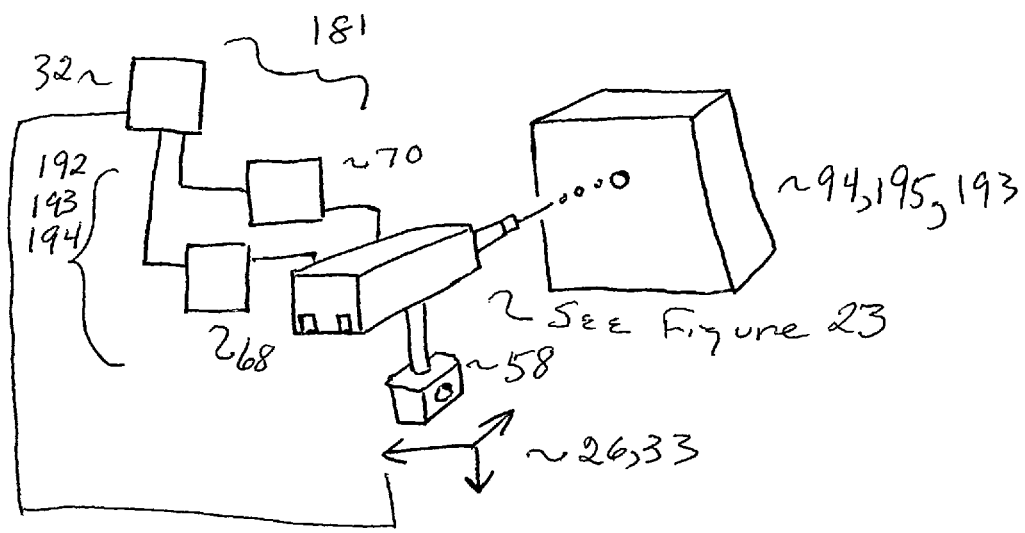
Figure 4 IBF Dispenser In MALDI + ESI Mode

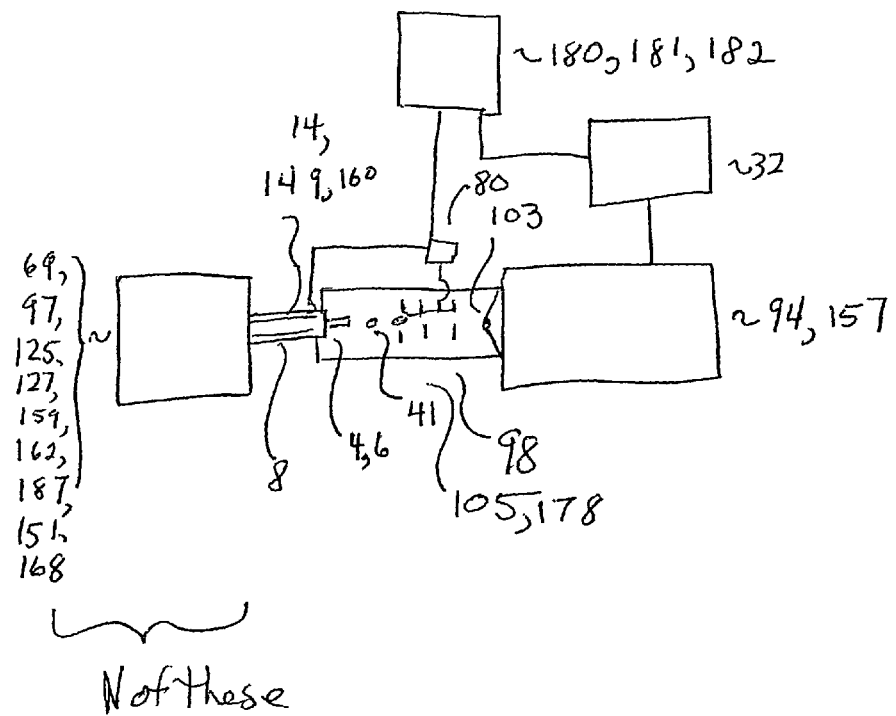
Figure 5 Generalized FBF Fluid Device Introduction, Treatment & Dispensing System IBF interfaced to MS, IMS, MS/MS or any other instrument w/without declustering tools

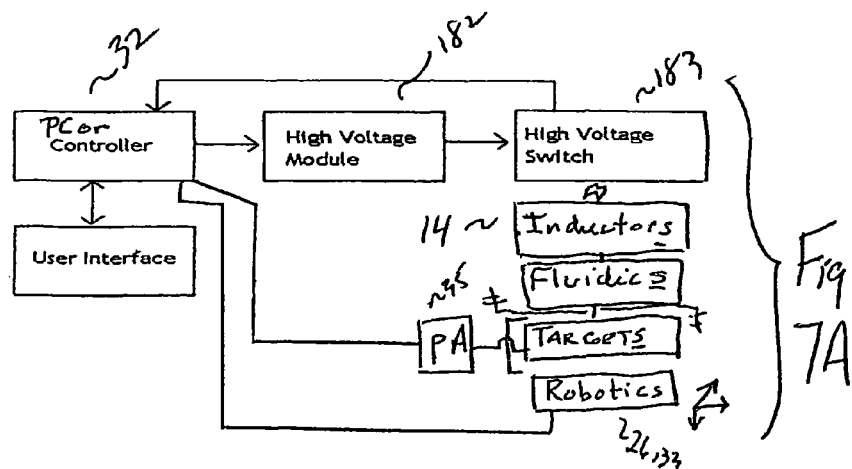
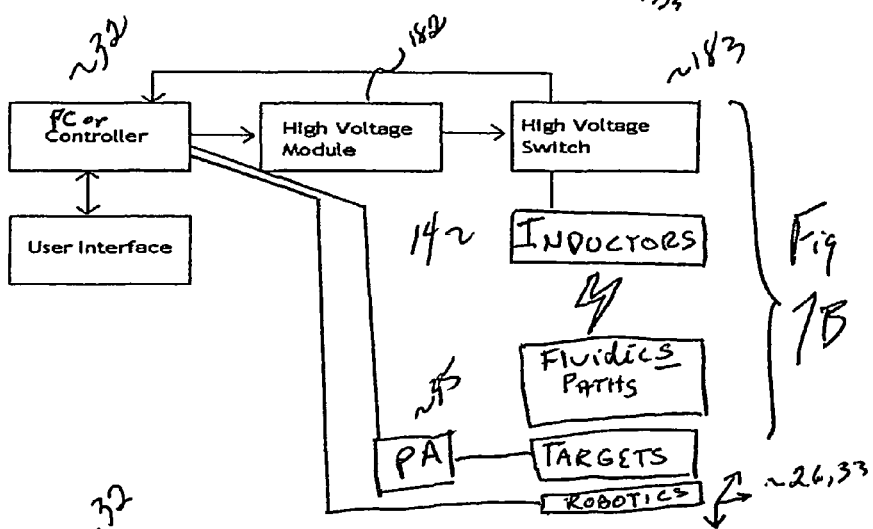
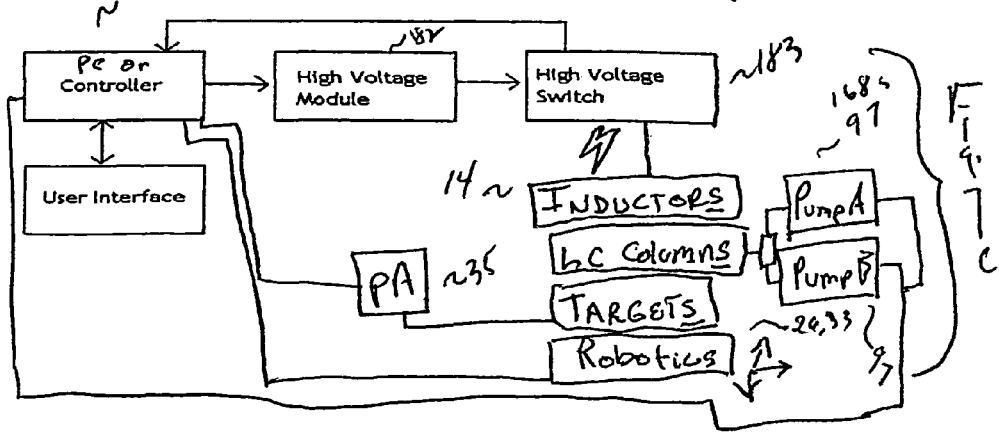

Figure 9. EMI/RF Shielded Induction w/Ty Plus user IBF Configs

Figure 10 ABF Pipette Tips Plus DART, ESI for MS Sample Introduction

Inductor parts and
circuit with optional gas
control

Array tape + Roche 384 poly-
pipetter or Nanostream
Syringe pack with Bilocal
Bipolar Programmed Energy App.

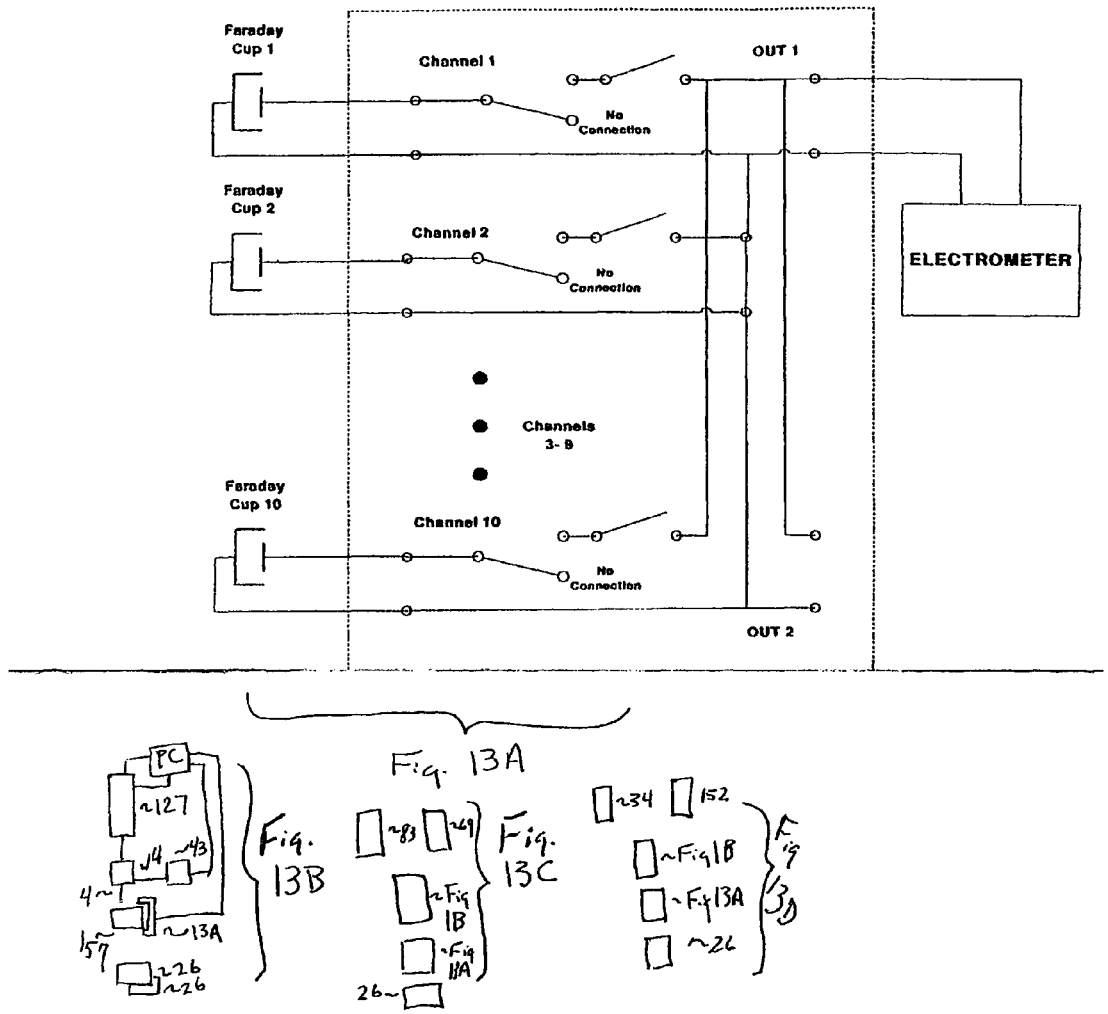

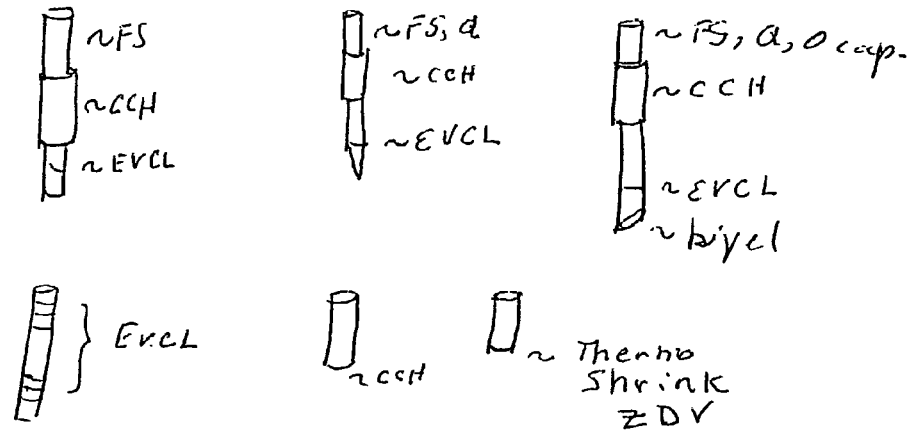
FS - fused silica     Q = quartz
CCH = color coded holder, PEEK
ZDV = zero dead volume union
~ conical compression fitting for polymeric device
Figure 14     Color, Laser, Other Coded
Fused silica, quartz tips, straight, bivelled, bi-beveled, coated w nanoparticles, more.

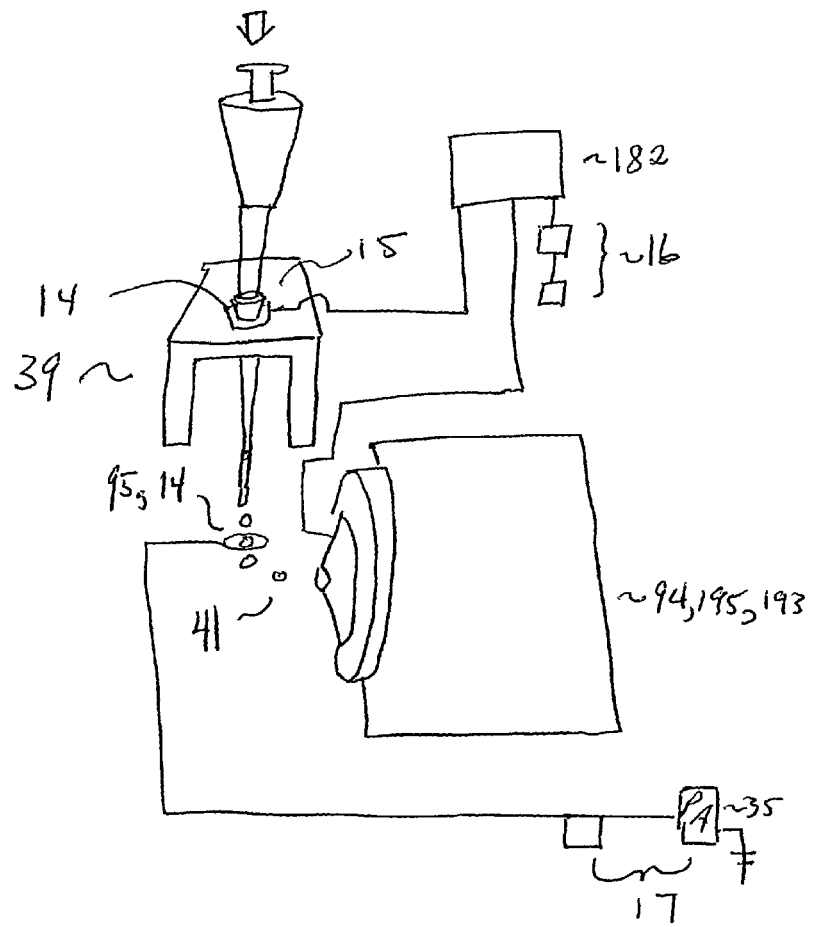
Figure 15 Pipette, G2 Gilson
MS w/a IBF
Wake Up

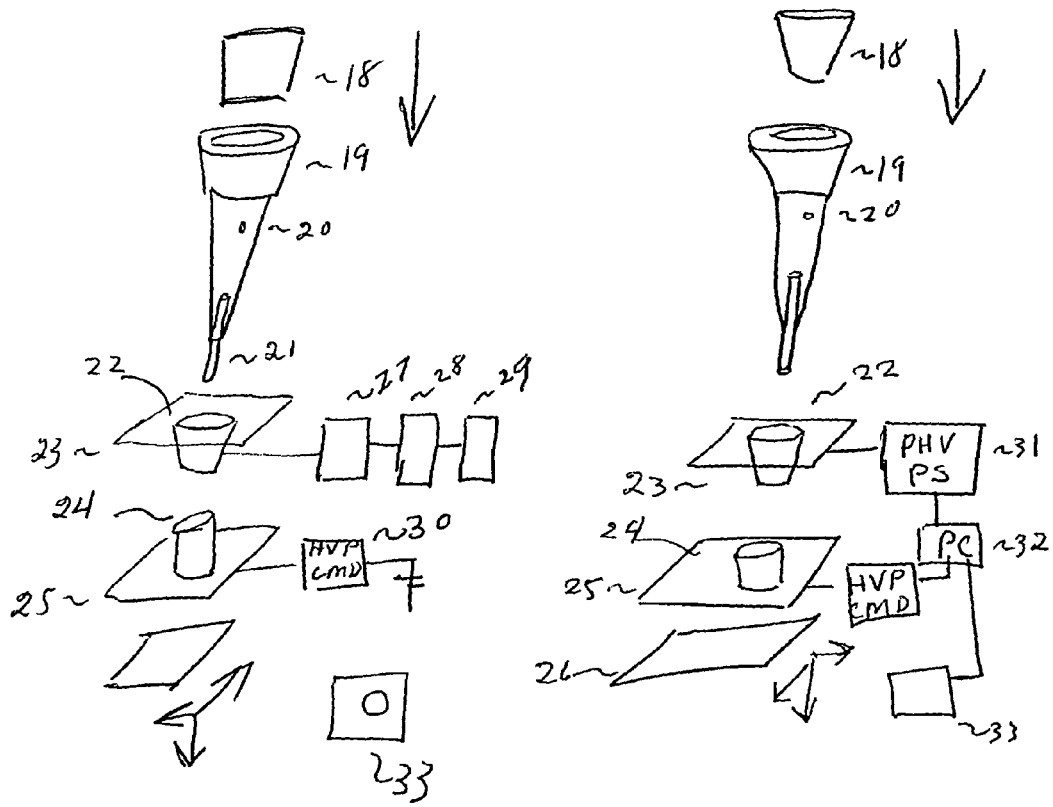
Figure 16 Analogue & Digital nanoliter/other pipette tips

8 Channel Analogue/Digital IBF
Pipette with multicurrent
capability

IBF Pipette w/ Analogue + Digital
Power Options, One Being dipolar,
Bilocal w DC or DC RF option Nanoliter IBF Pipette w/ Air Displacement Pump 20A
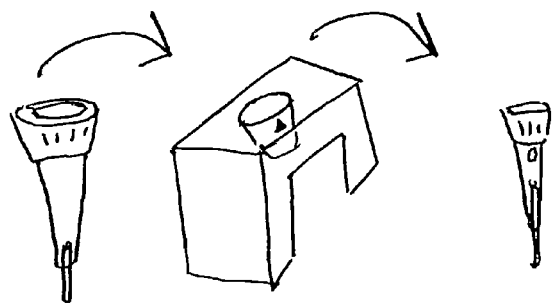
nL pipette tip + hole
puncture device + process
20B
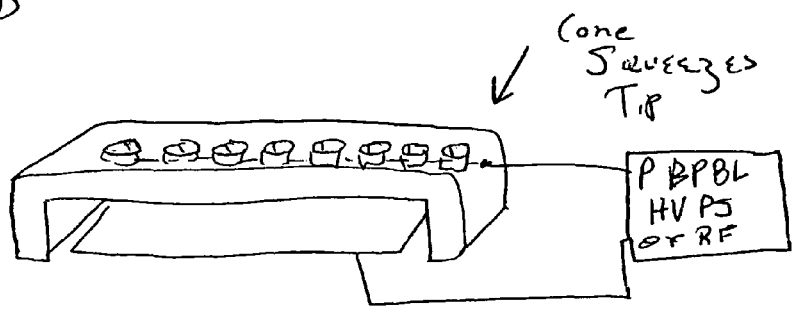
Figure 20  nL pipette + devices

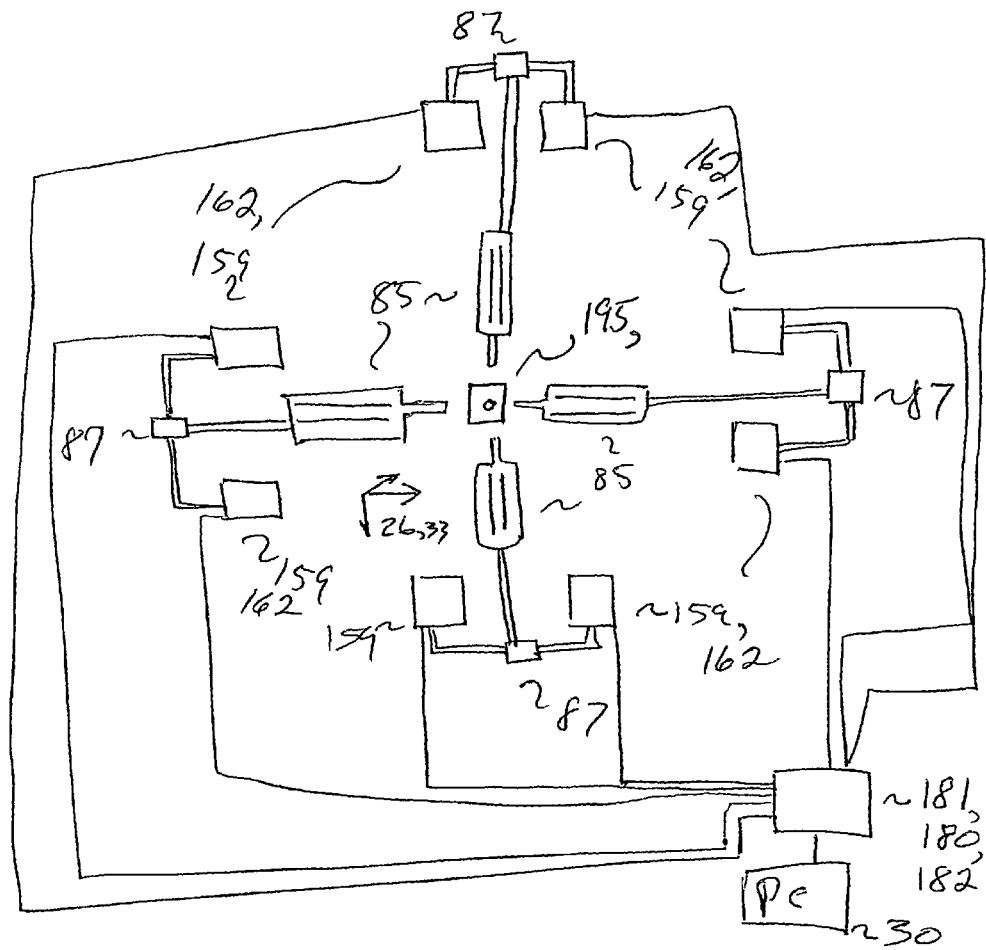
Figure 21 Parallel UPLC into MS, Multiplexed

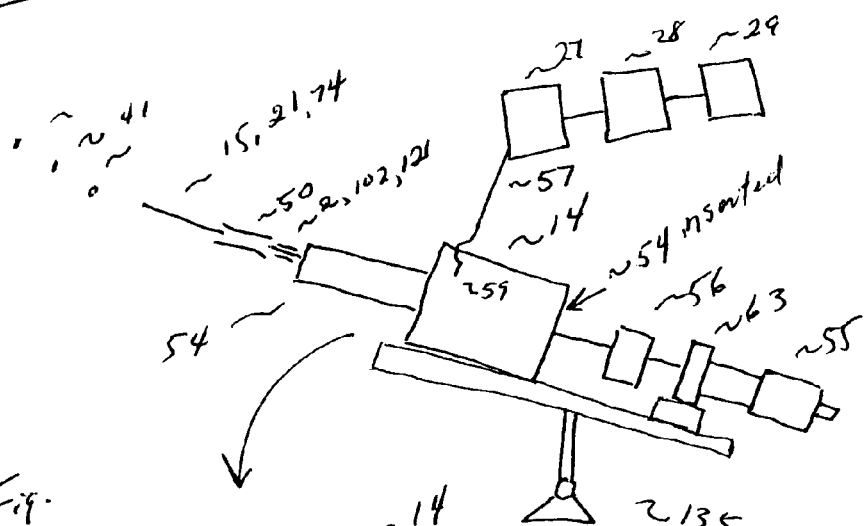
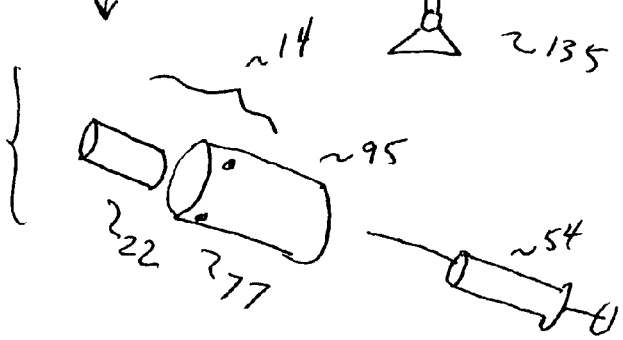
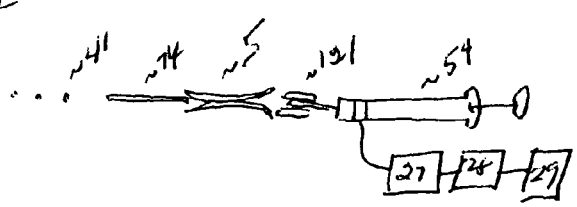
Figure 22 Analogue inductive nanoliter, microliter syringe IBF nL syringe, manual nanoliter Cool Wave® Syringe Figure 25 Polarity Switchable Charged polymer manufacturing Device.

Switchable, Polarity & Energy
Dispensing & Liquid Movement
Dispensing Device

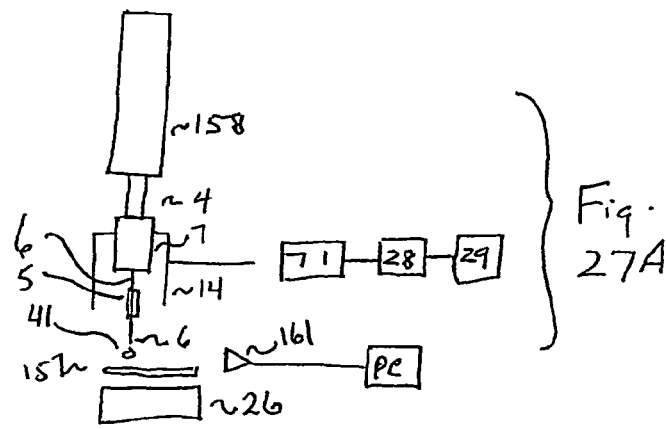
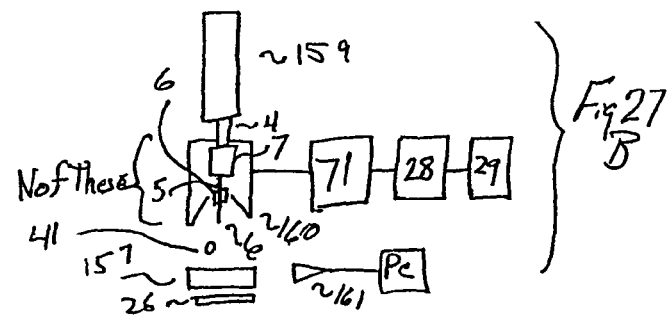
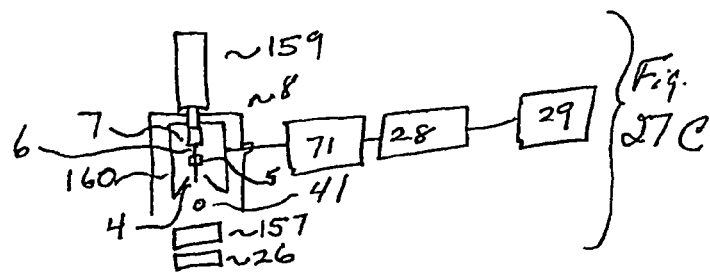
Figure 27 IBF induction, dispensing treatment, introduction + measuring device N Channel Ultra high pressure sample preparation

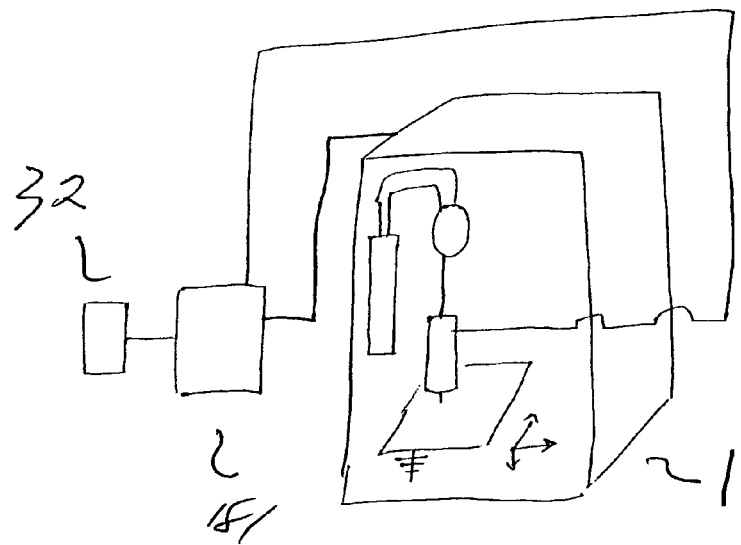
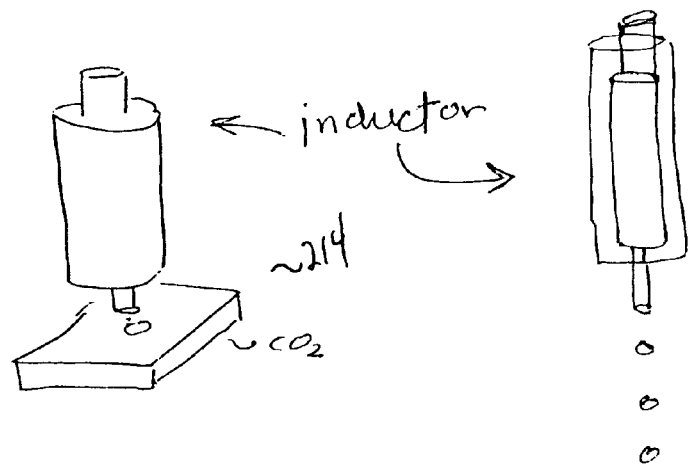
Figure 29 Spark Holland Alias, IBF Liquid LC, Dispensing Treatment Device

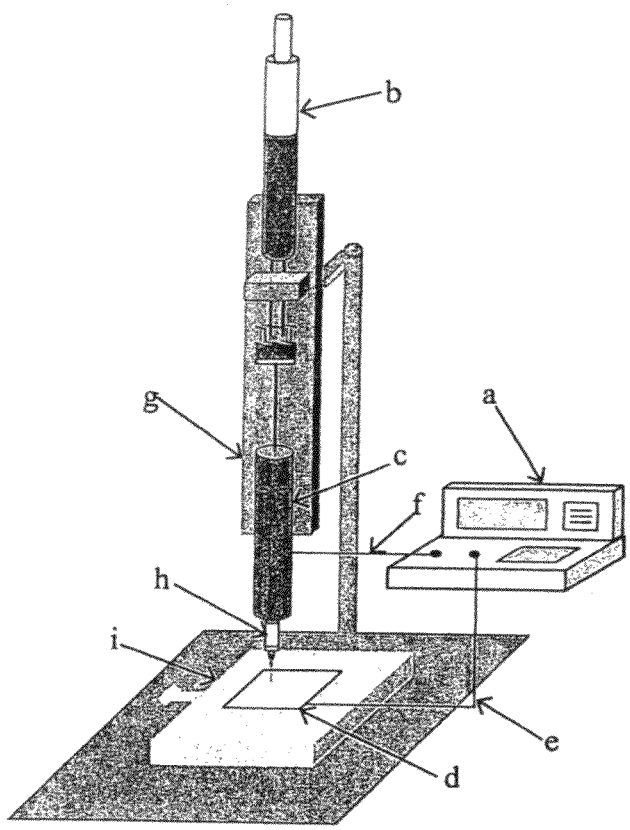

Schematic of a portable IBF nanoliter spotter for droplet deposition: (a) power supply module, (b) micrometer, (c) nanoliter wave inductor, (d) stainless steel MALDI plate, (e) electrical wire connected to ground, (f) electric wire connected to high voltage, (g) syringe holder, (h) syringe with a chemically treated capillary tip, (i) x-y adjustment stage.

Figure 30
"Manual" nL, uL syringe
w/ Programmable digital
HVPS. See Circuits 1, 2, 3 + 4
for driving electrical energy.

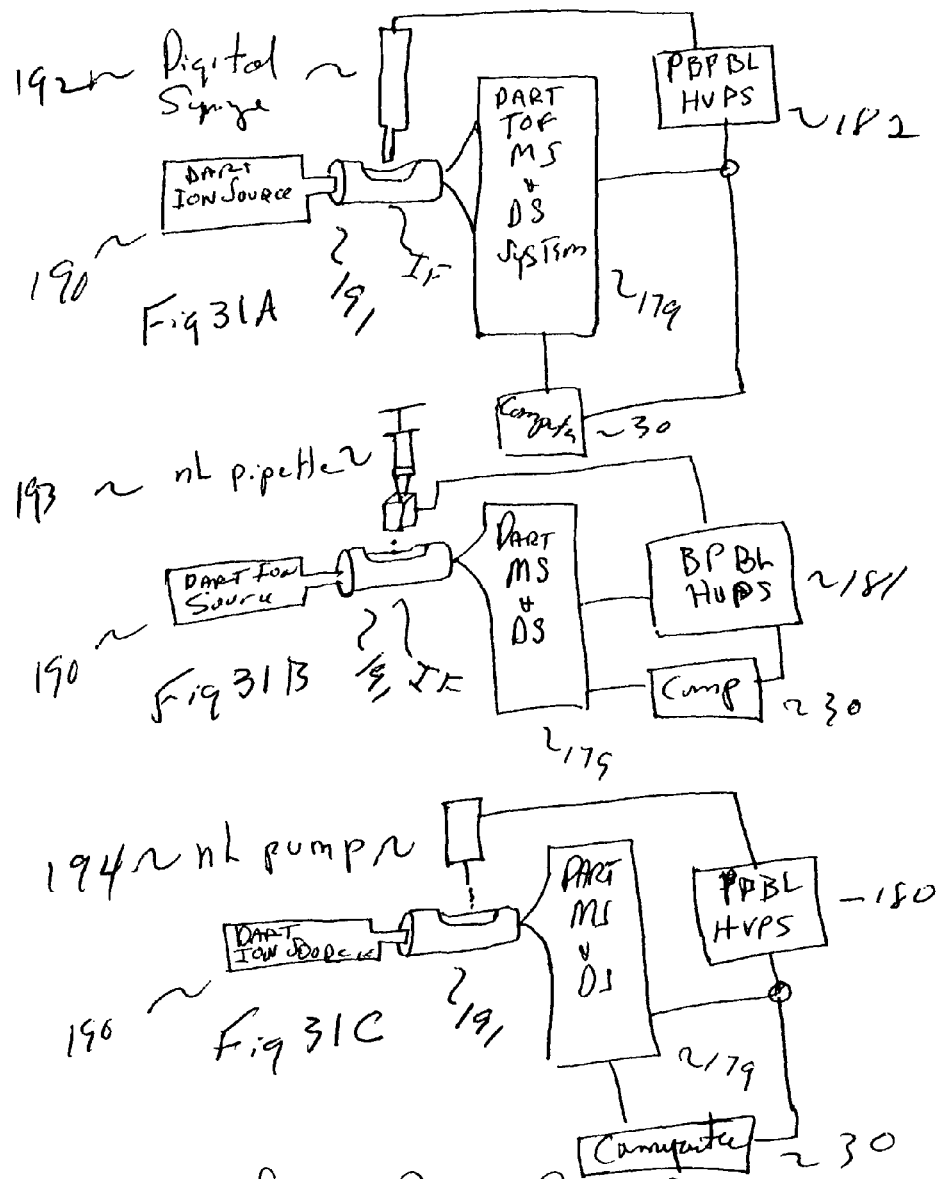

Figure 32  √BF, Douglas Array
Tape w Nanoscreen Dispenser
Optional + Roche 384 Pole-
Pipetter (4) Multiplexed MS non conductor    conductor Figure 33 nL pipettes into DART or other MS, MS/MS, IMS/MS or ESI or other sources

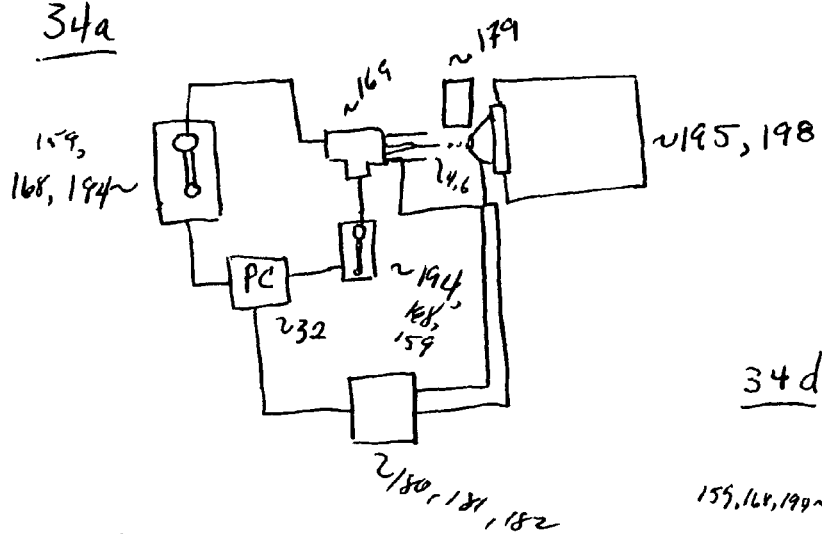
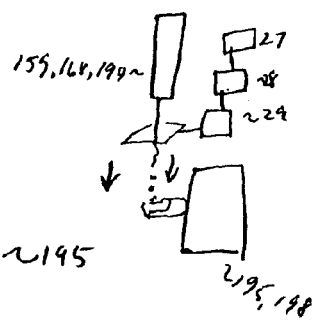
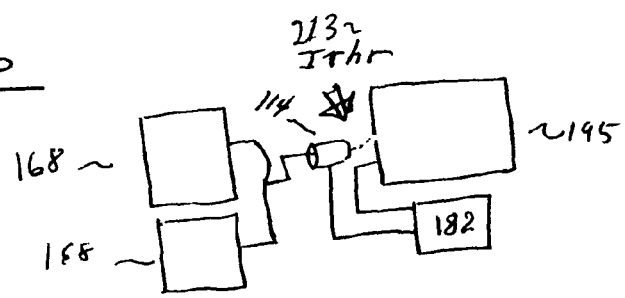
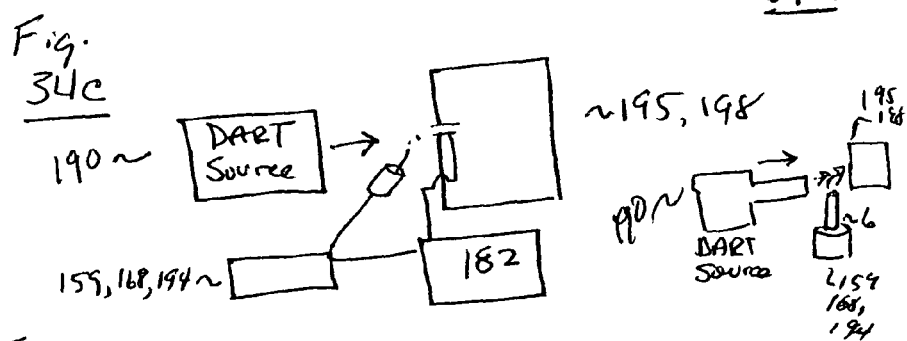
Figure 34 nL pump + mass spec, DART, DESI + MS TOOLS plus direct capillary introduction.

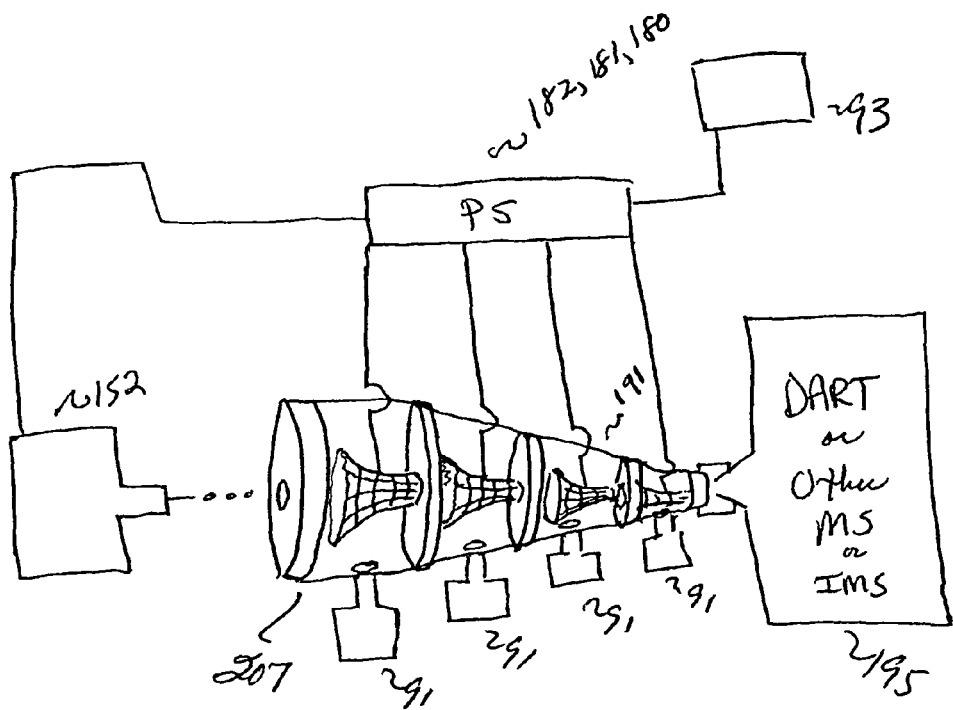
Figure 35, Neutral Pump Away Liquid Drop Accelerator w/ 4 Scram Cones, Differentially Pumped

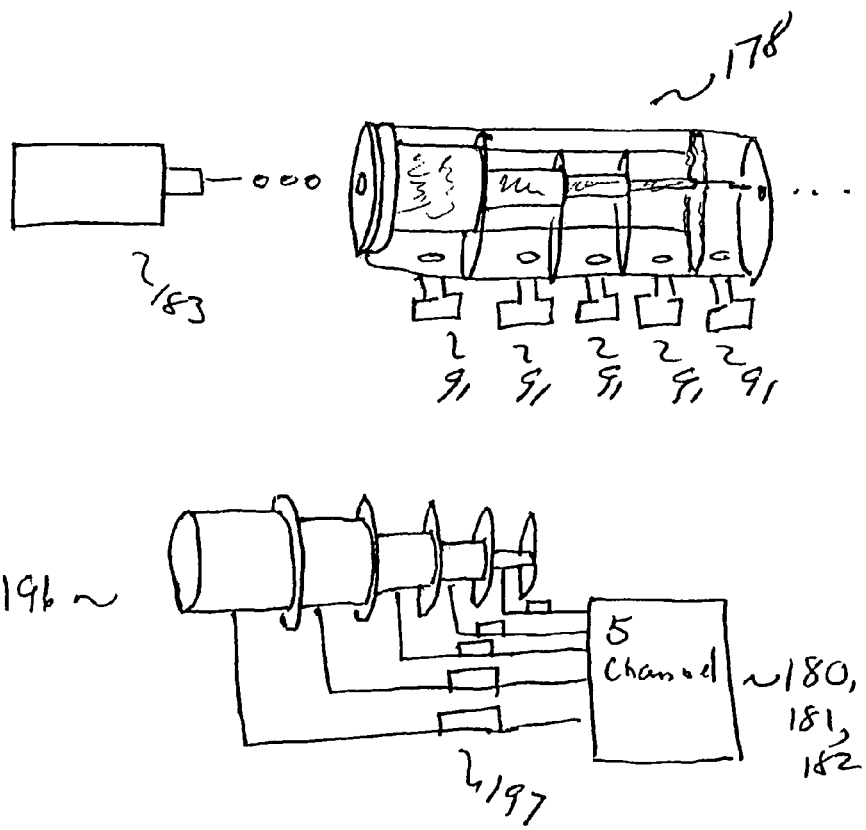
Figure 36 Gas Demod + Accelerator

Multiplexed MS or
Instrument System

Figure 38 Four channel LC/MALDI

IBF BASED LC/MS Programmed
Interface, Programmed Flow, or
Discrete Drops

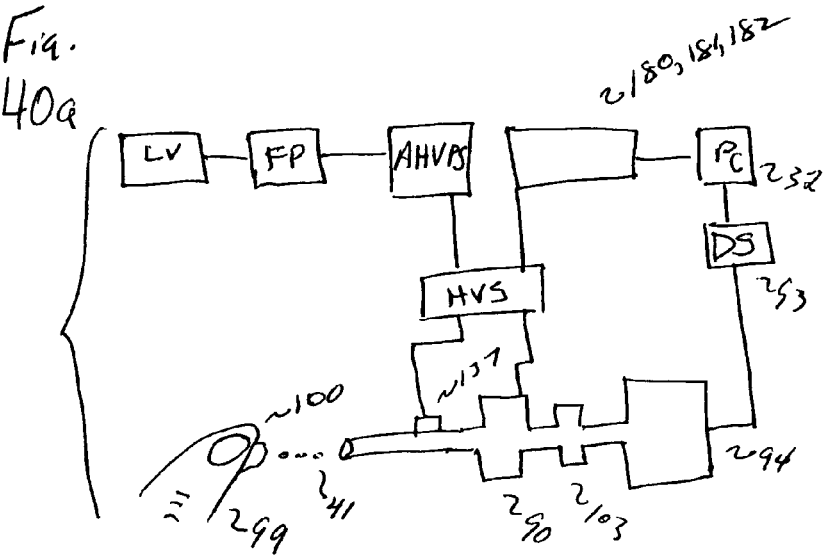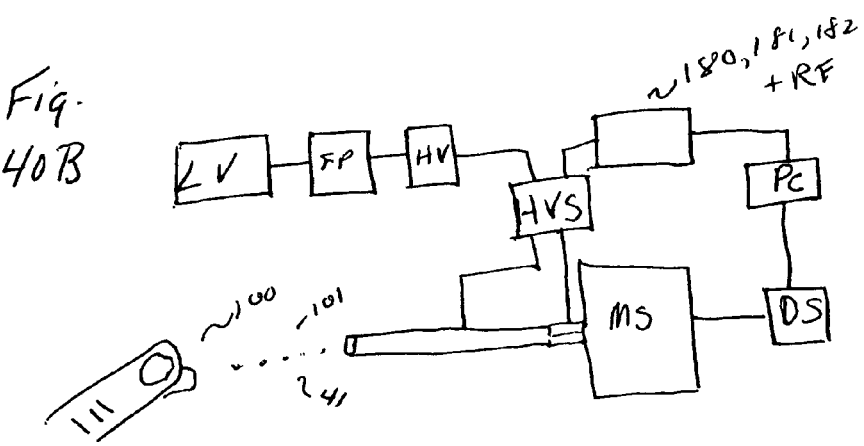
Figure 40 Human Sampling Device

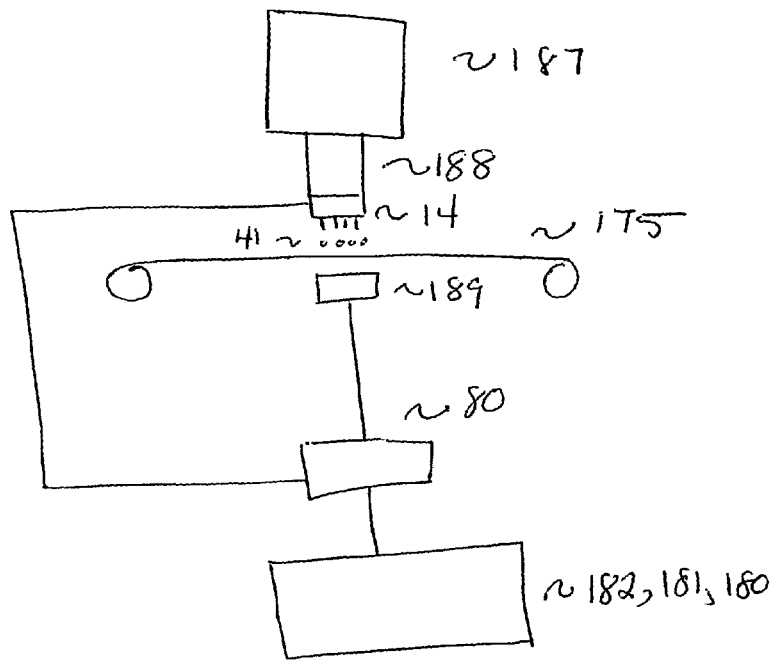
Figure 41 N Channel Programmable Dispenser Onto Plastic or Other Tape.

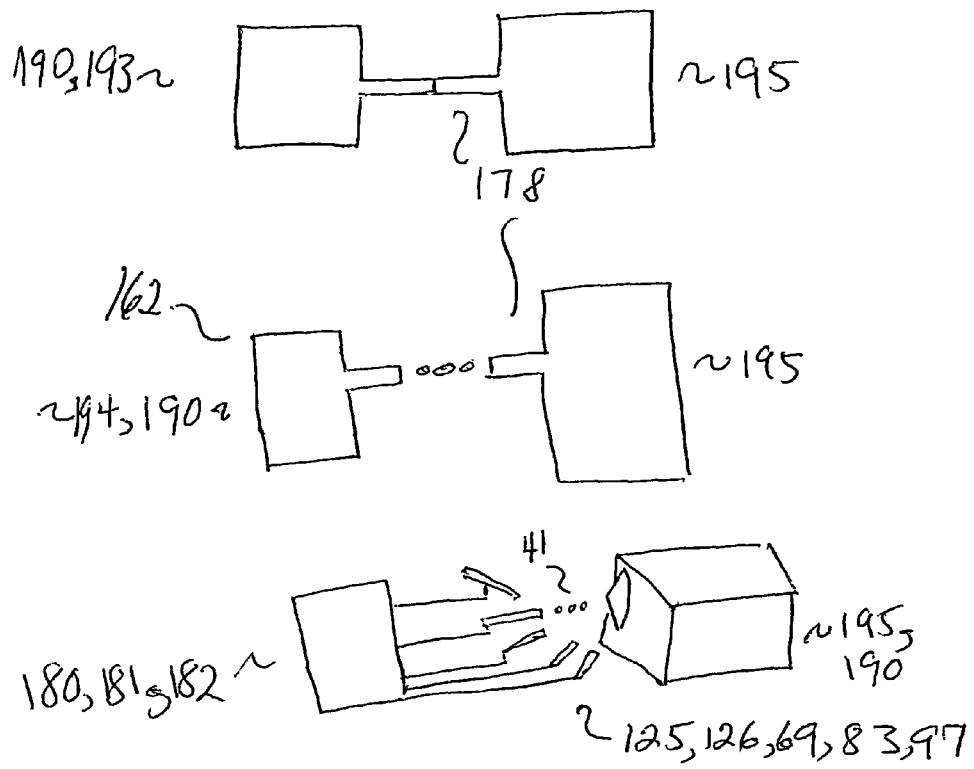
Figure 42 MS with IBF and Declustering Unit

RF Dispensers, RF energy is used to power drops to targets. Optional DC energy can be applied as well.

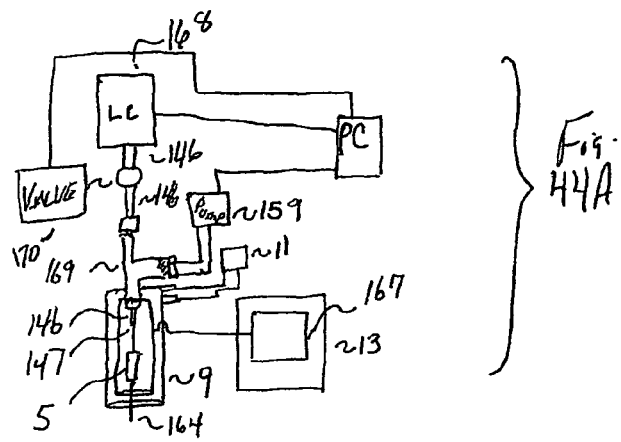
Fig. 44A
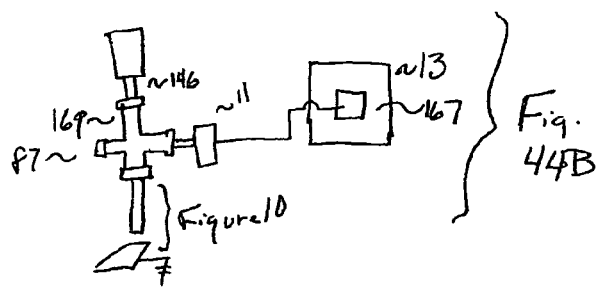
Fig. 44B
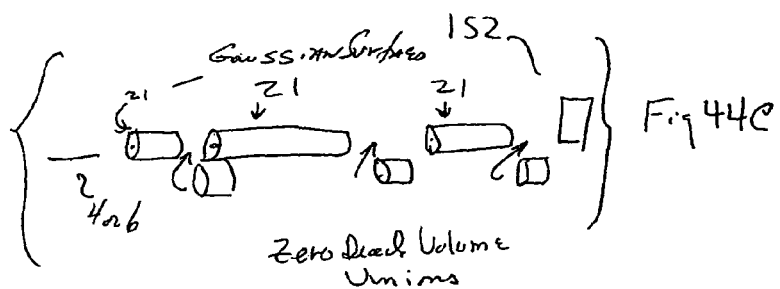
Fig 44C
Figure 44
Microprocessor IBF System
with ZDE Union.

Figure 45 nL dispenses onto humans & human parts

Figure 46 N Channel Unioso a Multiplexer for DART or Other MS.

Accelerating Denuder
* IBF Dispenser

Charged Polymer Manufacturing Device nL Pipette tip with selfing healing holy via compression DL Bipolar HV Power Supply
AND Array Tape Inductor

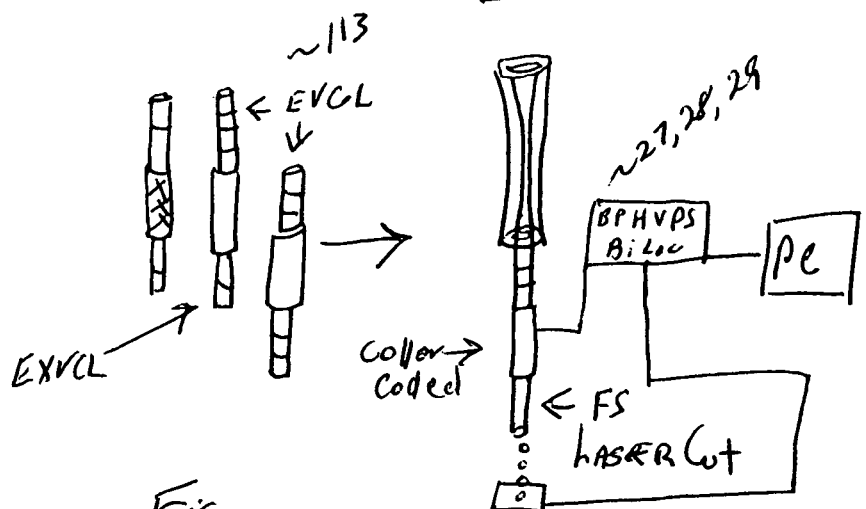
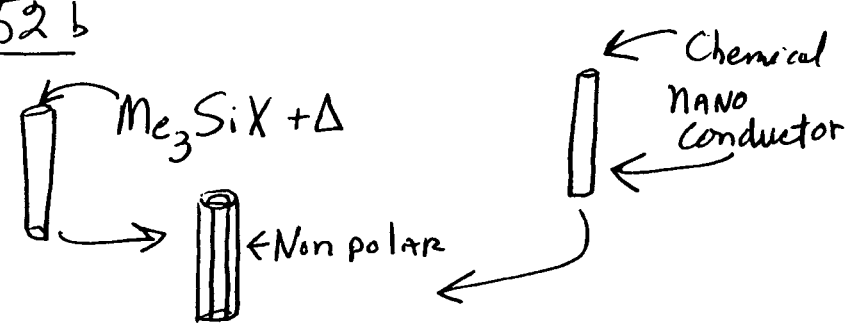
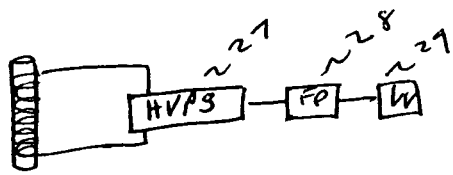
Figure 52
Dispensers & Tips

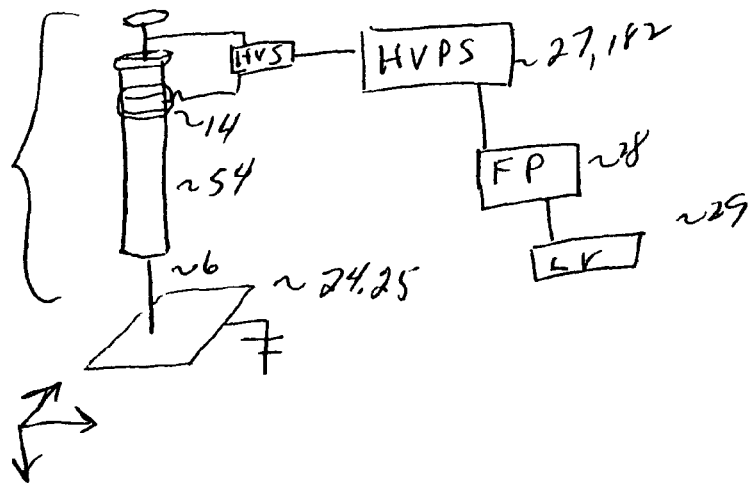
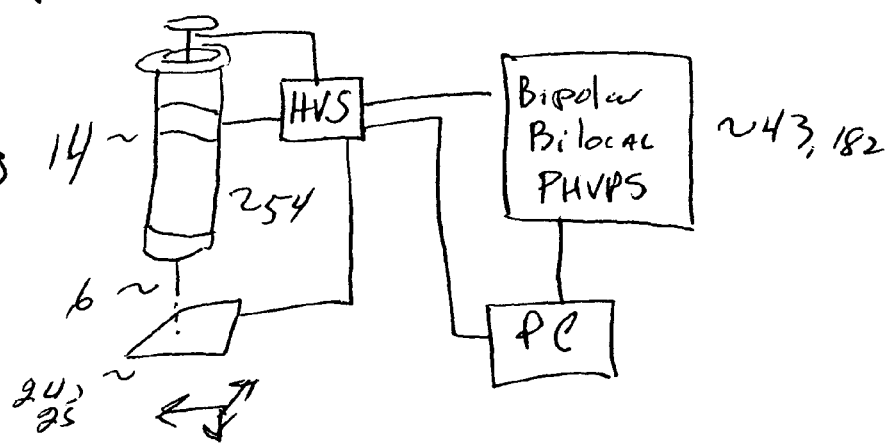
Figure 53
Inductive Conductive Analogue (A)
Digital (B) Syringe

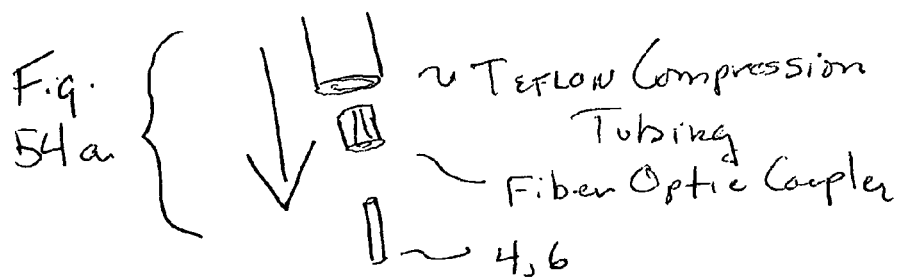
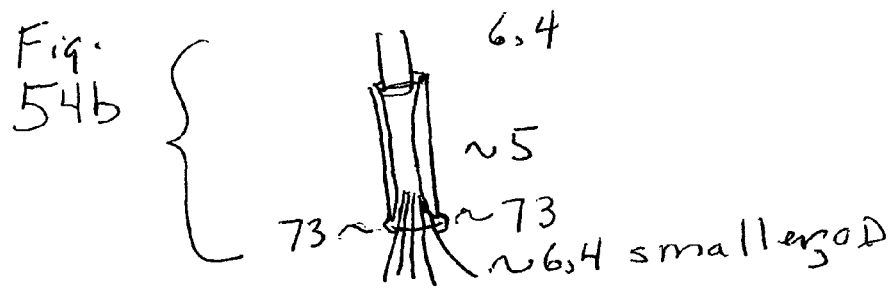
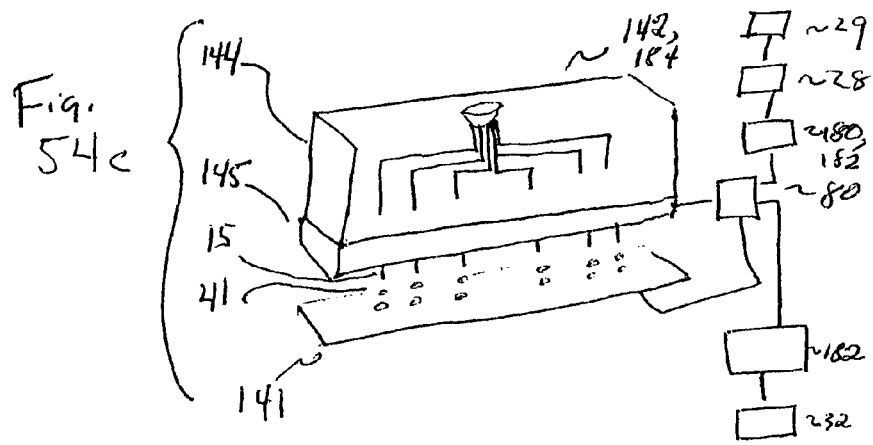
Figure 54 N fold chip based IBF Dispenser with Tips, Manifold Hand held nL, uL Syringe

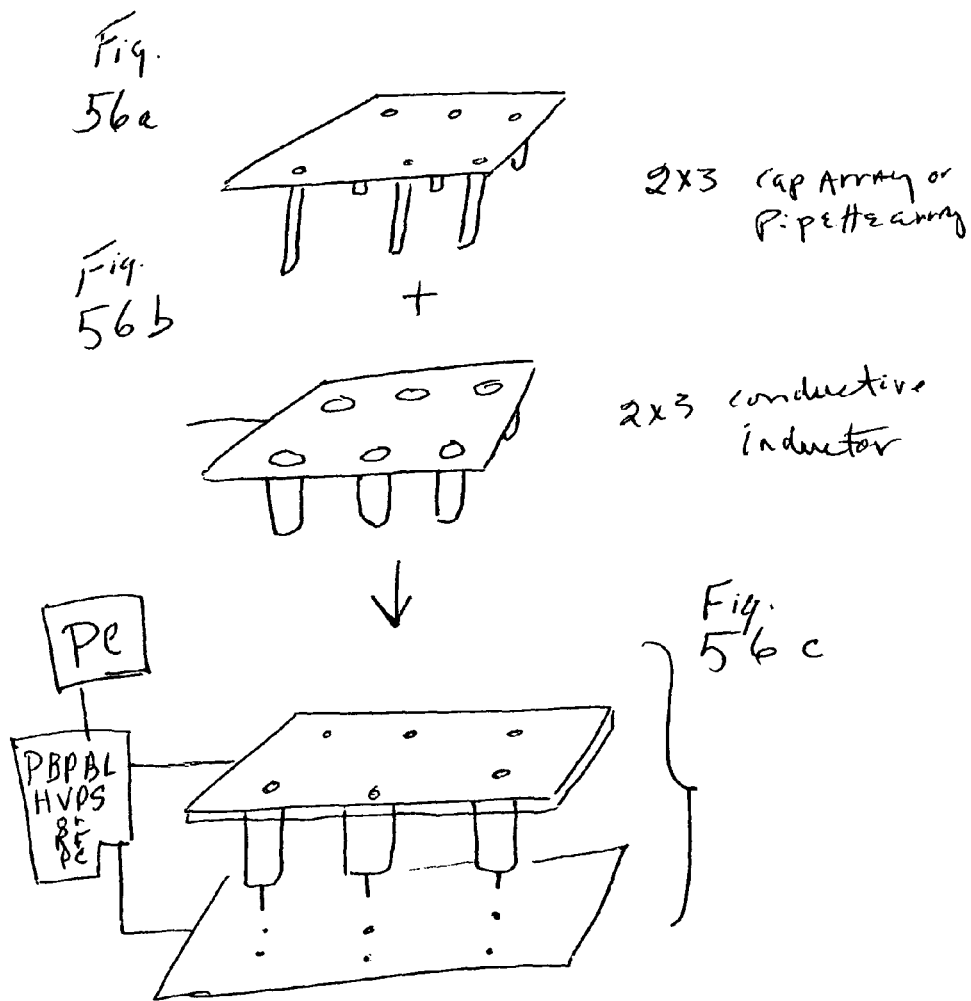

Fig. 57a
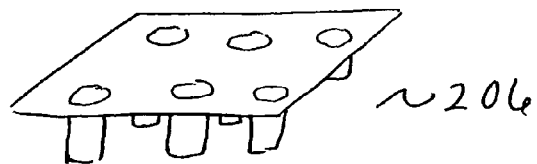
~206
Fig. 57b
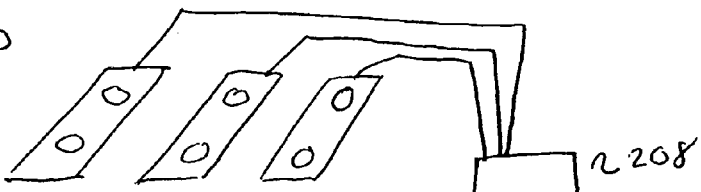
~208
Fig. 57c
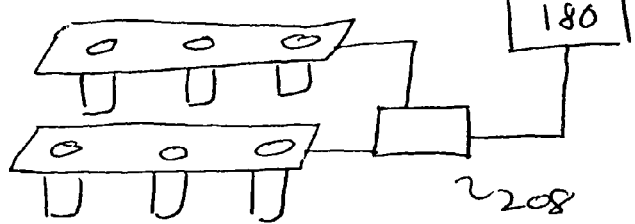
180
~208
Fig. 57d
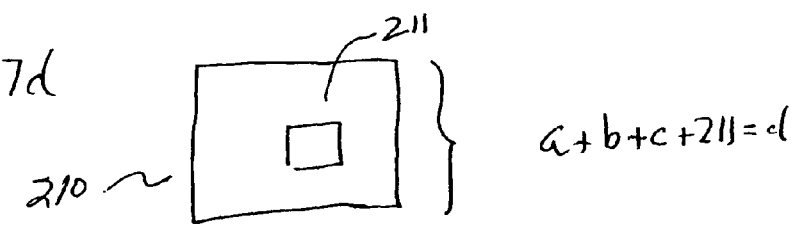
210
211
$a+b+c+211=d$
Figure 57
OBF Lumen Selectable
Dispensing + Volume Measuring Device

ENHANCED IBF, HYBRID, N-CHANNEL, X-LOCAL, Y-ENERGY MODE, Z-COUPLED NESTED GAUSSIAN SURFACES FOR LIQUID(S) DISPENSING, LIQUID(S) TREATMENT, LIQUID(S) INTRODUCTION AND SOLID(S) PRODUCTION VIA INDUCTION BASED FLUDICS METHODS AND APPARATUS

CROSS REFERENCE TO RELATED APPLICATIONS

This application is a continuation-in-part of U.S. patent application Ser. No. 11/137,254, filed on May 25, 2005, now U.S. Pat. No. 7,749,447.

BACKGROUND

Accurate and precise liquid movement or transport of dispensing across the macro, micro and nano worlds to a destination is of interest in countless areas including: drug and liquid product manufacturing; proteomics; genomics; bio and other agent detection; forensics; home and other health care; environmental and other areas and manufacturing of all types. The ability to accurately and precisely transport liquids can be employed to manufacture drugs or prescriptions; prepare samples for chemical analysis or for medical diagnostics, bioagent detection or handling or for forensics testing; to place chemicals, drugs or samples onto food, plants, animals humans or other objects or into scientific or other instruments or to perform isolation and purification functions; such as, filtration; solid phase extraction and liquid chromatography. The ability to manipulate small and large quantities of liquids using electric fields has other lesser known potential including: manufacturing new entities such as electronic components; frozen charged functionalized chemical entities that we have called nanoliter-sicles, repairing crystalline optics for large lasers and increasing the dynamic range of solution transport to existing pumping systems of diverse types. Devices that transport low quantities of liquids for such purposes have historically been largely mechanical in nature and they include: microliter syringes of all types; capillaries with attached bulbs; multi-channel pipettes and many different types of common pumps. More recently other devices have been applied to transport small quantities of liquids for various purposes including: piezoelectric devices; ink jets and other electromechanical devices. Such devices are not capable of dispensing liquids and performing useful functions across the macro, micro and the nano regimes (i.e., from mLs, to uLs to nLs to pLs to fLs) singly or in parallel with one source of energy. Either they cannot accurately transport the liquids across such a dynamic range or they have adverse properties including: inability to overcome adhesion and/or cohesion of small volume of liquids or liquid drops adhering to surfaces and as such they must touch off the liquid possibly contaminating the liquid or target, the device or both. Alternatively, even when for example low volumes of liquids are produced (but not higher volumes) they are not directed by the drop producing process and they can take trajectories that are not directed to locales causing errant location dispensing. Also, all low volume dispensing systems have large dead volumes, are complicated, and expensive in design and requiring at least one energy source per channel. Also they can exhibit have adverse electrochemistry; produce joule heating; or combinations thereof; that impact reliability and cost. Also, such devices again, cannot create and energize liquids, creating either drops or sprays, launch (i.e., push or pull) such drops or sprays to targets through the air as it actively directs the liquids trajectories to locales or targets that can be non-conducting or conducting without touching the target as it provides the energy to overcome the adhesion and cohesion of a liquid or liquids in drop, spray or hybrid form on the nested gaussian surface, N channels at a time with a minimum of one source of energy and optionally more than one.ni.

Technology that we have called induction based fluidics can make a simple capillaries of channels dispense liquids over more than nine order of magnitude and it has massive application space in matrix assisted laser desorption ionization mass spectroscopy in cancer diagnostics, polymer characterizations, and many other areas of health care and basic research and in manufacturing of drugs and special entities and elsewhere.

We have patented (U.S. Pat. No. 6,149,815 and U.S. Pat. No. 7,749,447) technology that can dispense liquids as it also performs functions across a massive dynamic range of literally in certain configurations and energy from mLs to fLs that has no moving parts, no or little joule heating, no adverse electrochemistry (i.e., faradaic processes) and that can perform parallel dispensing, parallel solid phase extraction, parallel filtration, parallel LC and parallel instrument introduction and more using as few as one source of energy where for N channels where N can literally be a very large number, as it directs the liquid to targets. In more recent work, we have taken this patented tool set that we call induction based fluidics and we have expanded the capabilities to small, less complicated even handheld devices that can dispense, literally fly liquids, as it directs liquids in the uL, nL and pL volume range using off-the-shelf devices like microliter syringes, or modified pipette tips to developing totally new technology that can place nanoliters onto humans or make MALDI spot plates in parallel or manufacture charged frozen nanoliter spheres that we have called nanoliter-sicles that can be aspirated by charged on non-charged rods, and as we have merged this IBF technology into more traditional older pumps; so that, IBF can be applied in tandem to other pump technology gaining the benefit or IBF including a wide dynamic range, highly parallel dispensing and other sample treatment options, excellent volumetric and spatial accuracy and precision plus unique capabilities and significant advances to larger fields of application.

In summary, this application extends IBF where this liquid transport technology that can employ as little as one source of electrical energy alone or use multiple sources of energy in tandem to transport, launch or fly, move or dispense one or more liquids as a flow, drop or spray to non-conducting or conducting targets one at a time or in a highly parallel manner across the mL, uL, nL, p L and fL dynamic volume range as it directs or attracts the liquid actively or passively to precise locations on inanimate or animate targets whether they are conductors or nonconductors. When the nested, gaussian surfaces contain filters or frits, SPE media, chromatographic phases, or other functionalized media the device can perform functions on the liquids; such as, filter, extract, chromatograph, purify and place or otherwise transform the liquid or its contents as they serially perform the transport function in a parallel mode optionally placing the liquid onto a target or targets be they surfaces, containers, scientific instruments, chemicals, drugs, food products, plant, animal or human subjects or other targets as it provides one or more ways to quantify the volume, and locations of the liquid/s providing other ways to facilitate operation.

Because the physical movement of fluids is so elementary to so many processes in biotechnology, health care, manufacturing, daily life and other areas it is impossible to adequately address all applications of this matter transport technology.

SUMMARY OF THE INVENTION

Apparatus electrokinetically energizes and transports liquids to locales or targets through nested gaussian surfaces independently or optionally in a hybrid mode using electrokinetic and other energy sources; such as, plungers; siphons; pneumatic pumps, piezoelectric pumps, peristaltic pumps, ultrasonic pumps, thermal energy, gravitational energy, manual energy or other energy sources combinations transports or dispenses milliliter, microliter, nanoliter and picoliter quantities of liquids with an accuracy and the precision of a few percent without or with touching the target or targets using one nested gaussian surfaces or a series of coupled or joined nested gaussian surfaces which can have the same or different cross sections and which can exist in a singular or plurality of many similar or different coupled nested gaussian surfaces. Such surfaces can be handheld, mounted to holders in parallel or joined into a plurality of a series of such surfaces mounted and or otherwise attached to a robotic platform of x,z of other geometry such that electric energy can be applied to the surfaces individually or collectively via electric induction or via a direct wired connection to any nested surface or series of nested gaussian surfaces or to liquid contents thereof or optionally to any physically disconnected or physically connected target or targets where the gaussian surfaces or the targets can be made of nonconductors or conductors or any combinations thereof, as it uses passive or active surfaces to direct the liquid or its parts to targets be they vessels, surfaces, instruments, food, plant, animal or human subjects.

The apparatus consists of a unipolar or bipolar DC power supply which may be arc protected, current limited and optionally programmable coupled optionally to a RF power supply whose individual energy can be combined with the DC energy in any mixture and applied to the any gaussian surfaces or its electrically disconnected targets via induction or by direct electrical connection to any or all of such surfaces where the potential can be turned on or off using a switch in a ballistic manual mode or alternatively using a selector switch and a potentiometer or alternatively an auto transformer that can be employed to apply a constant potential or that can be manually changed in a positive or negative fashion to effect a dynamic change of potential or in a programmed by mode that uses a computer or microprocessor driven circuit to drive the programmable power supply or supplies that can take the applied potential from any value V1 to any value V2 using any C++ function or series of C++ functions applied to any gaussian surface individually or collectively or to any physically connected or disconnected target or targets. The apparatus further consists of surfaces made of conducting or non-conducting materials that can actively or passively form and direct the liquid as it emanates from the last gaussian surface prior to launching to the target or targets that may be charged or non-charged.

The device can optionally consist of various options to facilitate operation and to verify the operation of this technology including: a source of light to aid in visualizing targets such as lenses and LED which may optionally be fed from a fiber optic cable; a source of laser or other light to make spots of exact, known dimensions near adjacent to targets to aid calibration via machine visions techniques such as pixel counting; a foot pedal that can be employed to control the energy application to the devices or targets; a motorized plunger that can fit into the gaussian surface or surfaces to push the liquid to grow drops or otherwise transport or produce drops of flow for transport through media for subsequent transport to targets; coils or other current measuring devices to measure the charged liquid transport through a space from a gaussian surface verifying a dispense or optionally use machine visions techniques; such as, pixel counting of liquid blots on surfaces or video recording to further or independently verify the accuracy and the precision of liquid transport to a receiver or a surface; employ one disposable gaussian surface or more than one as the body of the device, as a tip or as the entire liquid holder; a series of selector buttons on the device or on the power unit an IR remote to control and to select the energy level and energy path of an experiment; mounted or detachable volumetric scales with lenses to visualize and measure the liquids; a charge station or stations where the one or more joined, nested gaussian surfaces can be electrically charged by direct connection to or by induction from a voltage source; assorted electrical attachments provide energy to any gaussian surface or its contents; compression and other fittings to join gaussian surfaces and disposable tips made of fused silica, polypropylene, quartz, PFTE, optionally equipped with frits, chromatograph or other media, and themselves potentially coated with PFTE, metals, polymers, or other inert or conductive material/s with or without electrical leads, a cradle that can hold the joined, nested gaussian surfaces, batteries, charging circuitry and circuitry to sense the liquid level or plunger position with alpha numeric LED and other displays, a holder or set of holders that can isolate the joined, nested gaussian surfaces from or optionally connect them to ground; compression, screw based or quick connect or zero dead volume unions to join or couple gaussian surfaces made of quartz, fused silica, polypropylene, PFTE and or coated there to with inert, metallic or non-conducting materials,

BRIEF DESCRIPTION OF THE DRAWINGS

FIG. 1 presents nanoliter induction based fluidic (IBF) dispensing devices, 5 configurations.

FIG. 2 is a bipolar, bilocal programmable HV power supply: manual and PC control.

FIG. 3 driving and counting digital nanoLiter Cool Wave dispenser.

FIG. 4 driving, counting digital nanoLiter Cool Wave dispenser, N channel.

FIG. 5 digital nanoLiter Cool Wave dispenser, N channel with fast msec relays.

FIG. 7 Three IBF configurations of fluidic, electronic circuitry.

FIG. 13 IBF dispensers using Keithley, other switch card for voltage mode.

FIG. 14 IBF tips.

FIG. 15 IBF pipette with current/volume measurement.

FIG. 16 IBF 8 channel analogue, digital pipette with current measuring capability.

FIG. 20 Pipette puncture device and squeeze holder.
FIG. 21 IBF nL pipette tips.
FIG. 22 IBF, nanoliter syringe.
FIG. 29 IBF Spark Holland sample dispensing and treatment device.
FIG. 30 IBF manual nL syringe, plus programmable controller.
FIG. 31 IBF, DART, DESI, other MS sample interface.
FIG. 34 IBF pump, DART, DESI interface.
FIG. 35 IBF dispenser with degassing, accelerating interface.
FIG. 36 IBF dispenser with degassing, accelerating interface with DC/RF modes.
FIG. 40 IBF human, animal, plant, other sampling device.
FIG. 41 IBF Array Tape dispensing system with BPBLH-VPS with DC/RF option.
FIG. 42 IBF MS interface.
FIG. 44 IBF microprocessor system.
FIG. 52 IBF nanoliter pipette and capillary tips.
FIG. 53 Inductive, conductive Analogue and digital syringes.
FIG. 54 IBF n fold chip based dispenser.
FIG. 56 Capillary, cylinder array.
FIG. 57 IBF, lumen selectable, dispensing and volume measuring device.

DETAILS

Figure 6:
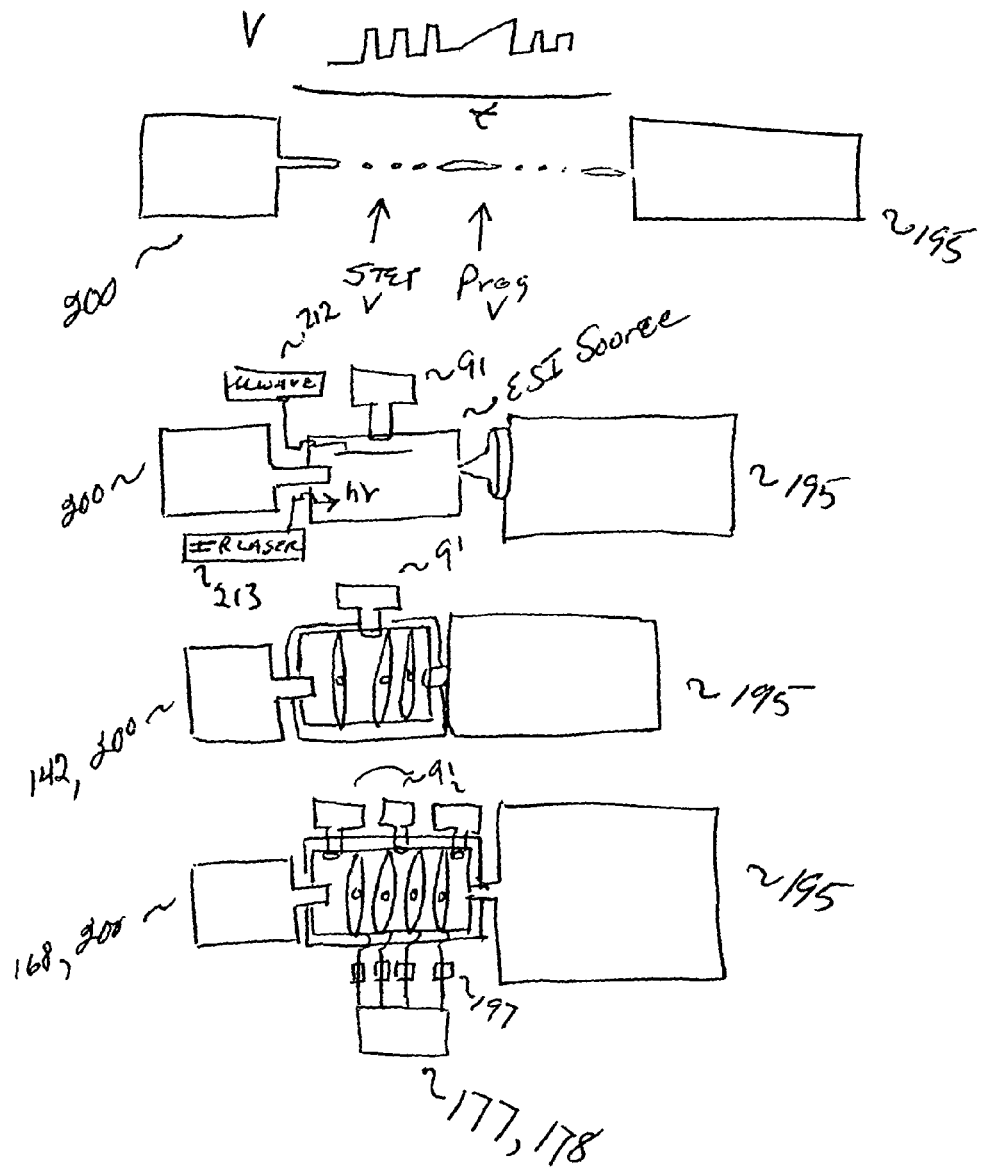
FIG. 6 IBF dispensers into any devices, instruments.
Figure 8:
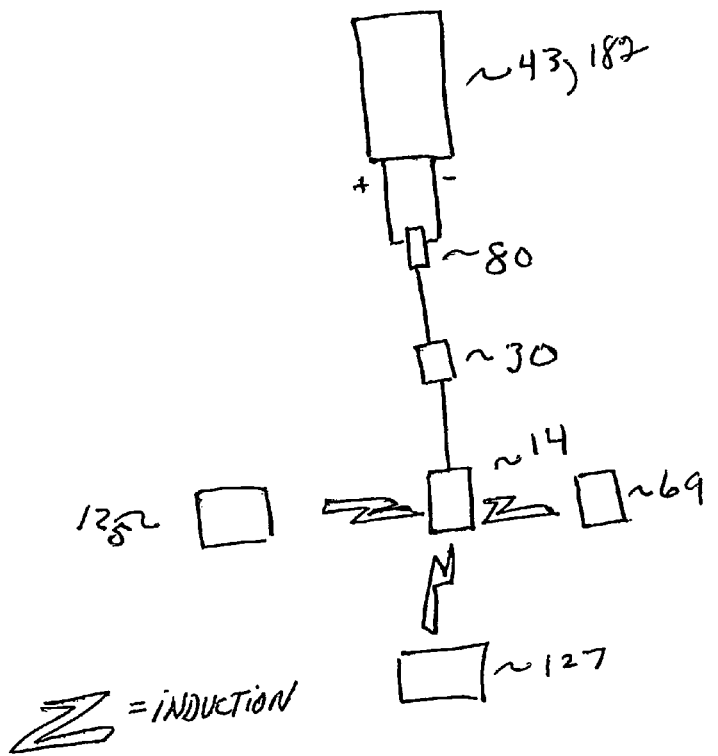
FIG. 8 Bipolar, DC/RF IBF systems for syringes, pipettes and pumps, generalized.
Figure 9:
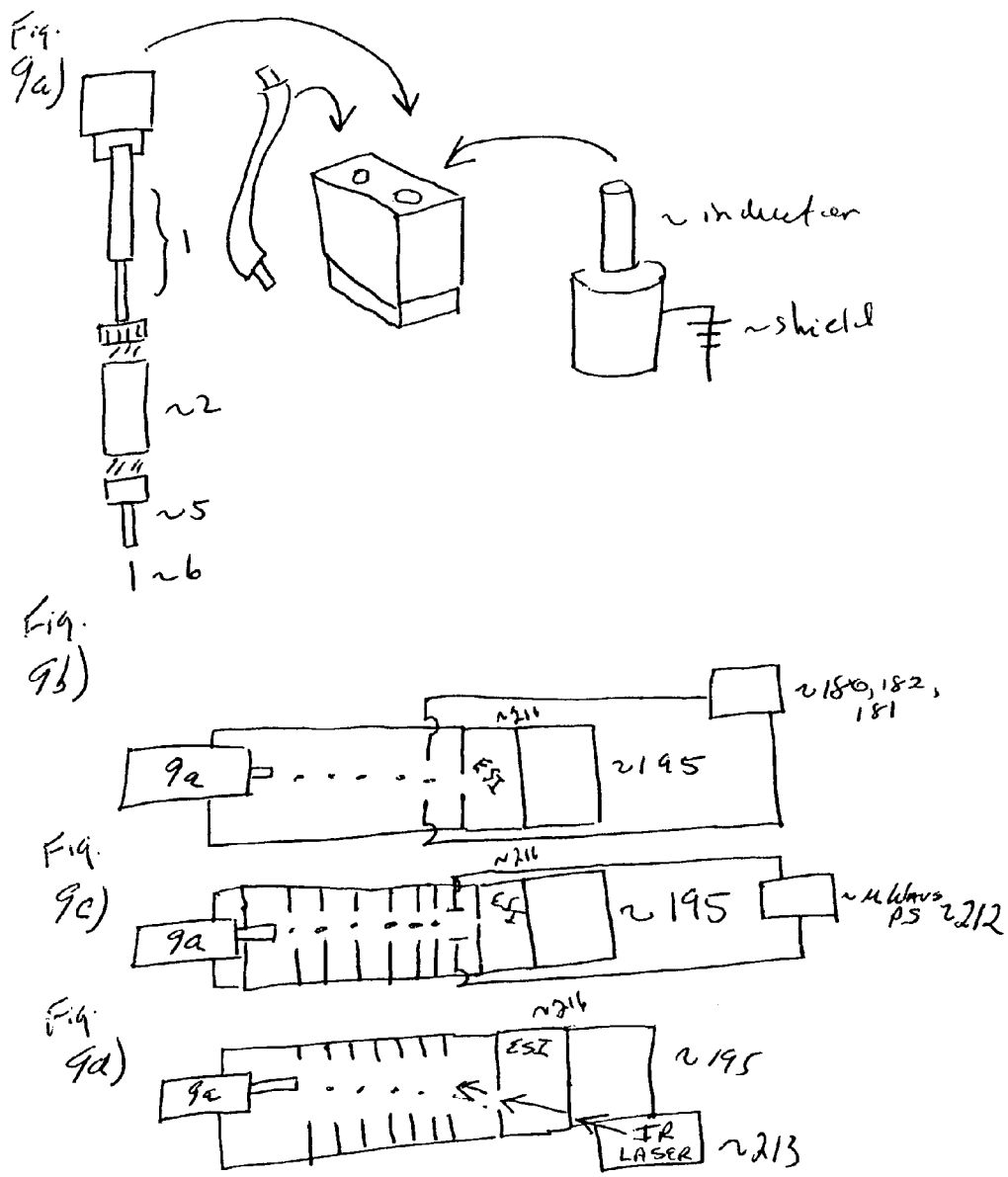
FIG. 9 Inductor with dispenser and EMI/RF shield.
Figure 10:
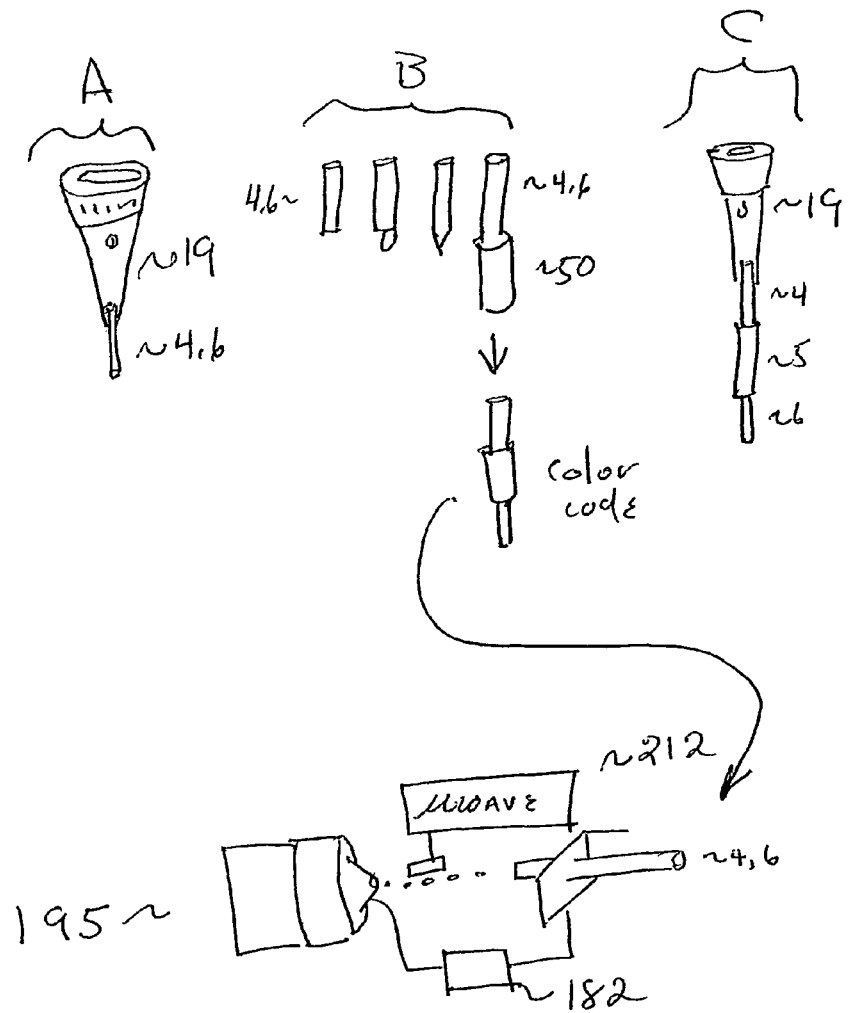
FIG. 10 IBF pipette tips, various configurations.
Figure 11:
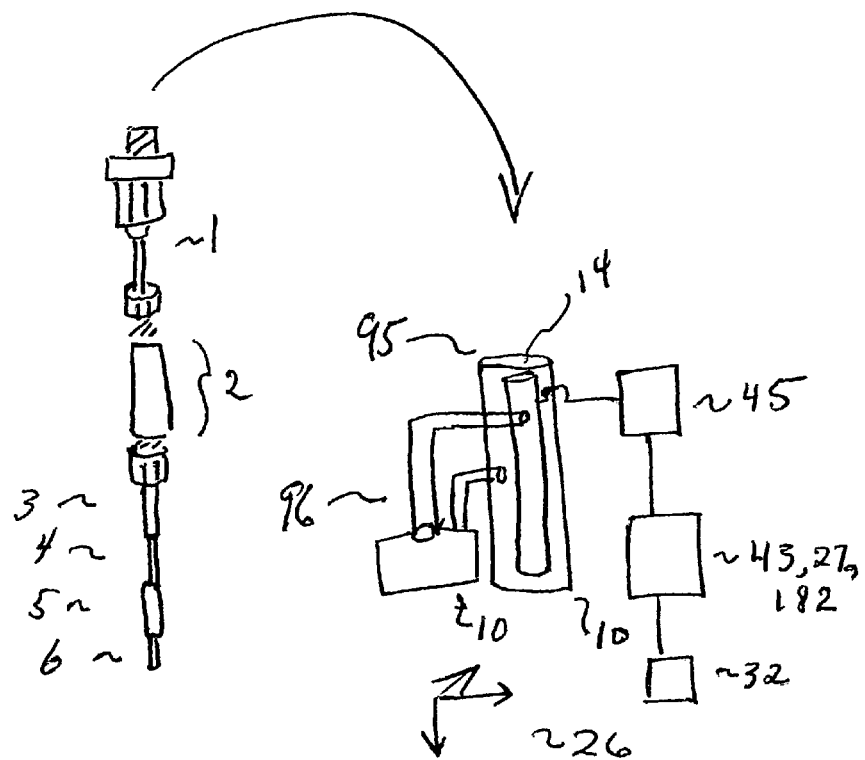
FIG. 11 Inductor with gas inlet options.
Figure 12:
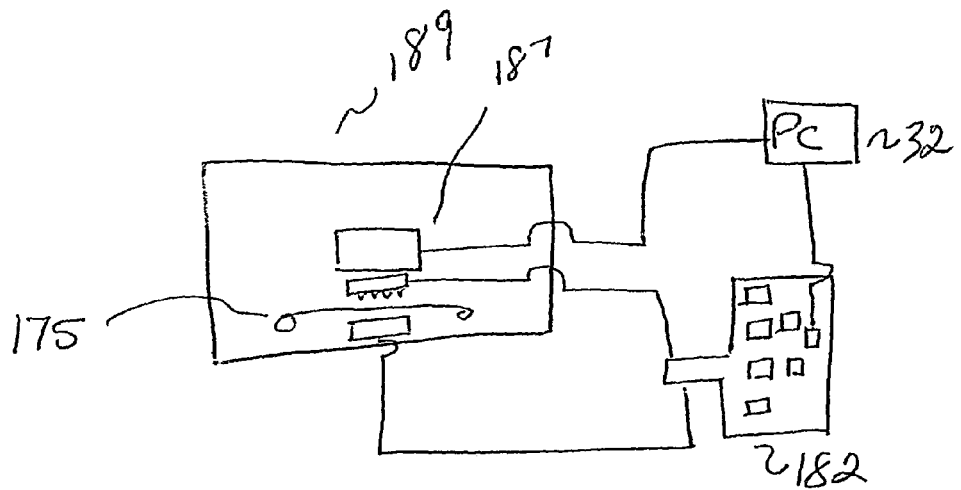
FIG. 12 IBF dispenser intoArray Tape, suing Roche Polypipettor or optionally NanoStream 384, 1536 Syringes and HVBPBL PS.
Figure 17:
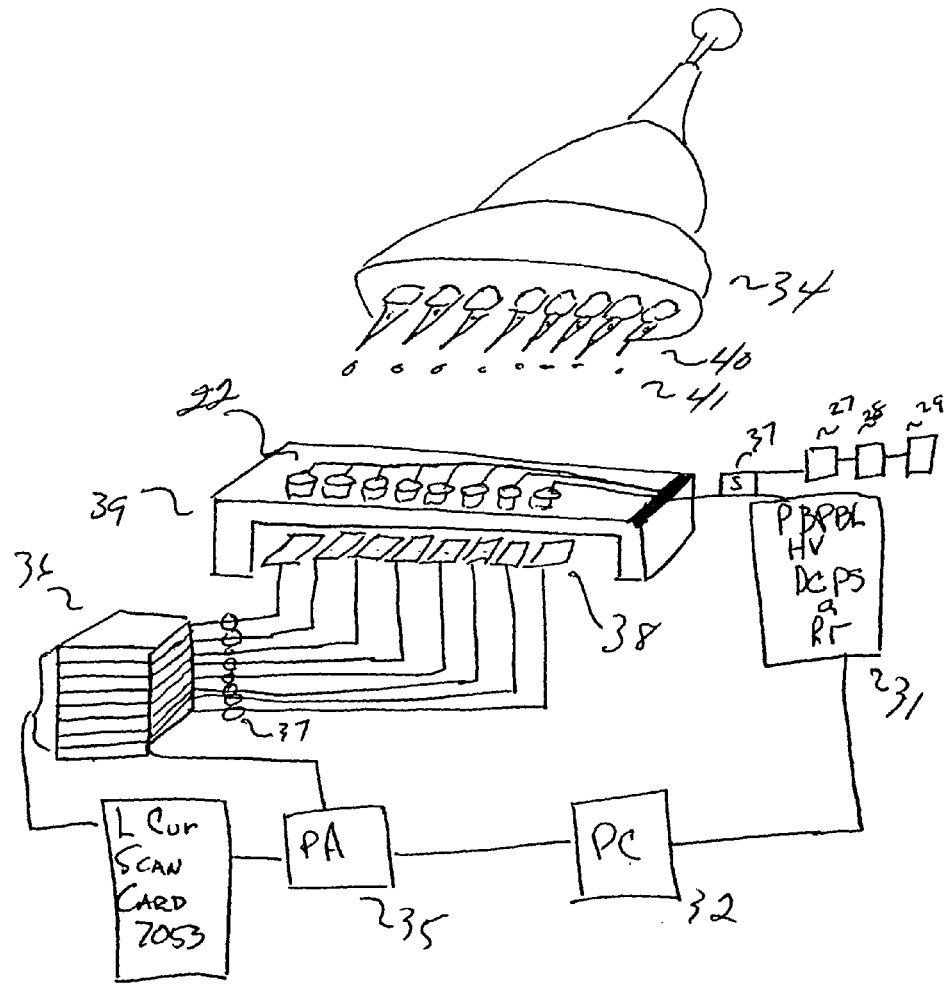
FIG. 17 IBF, 8 channel pipette.
Figure 18:
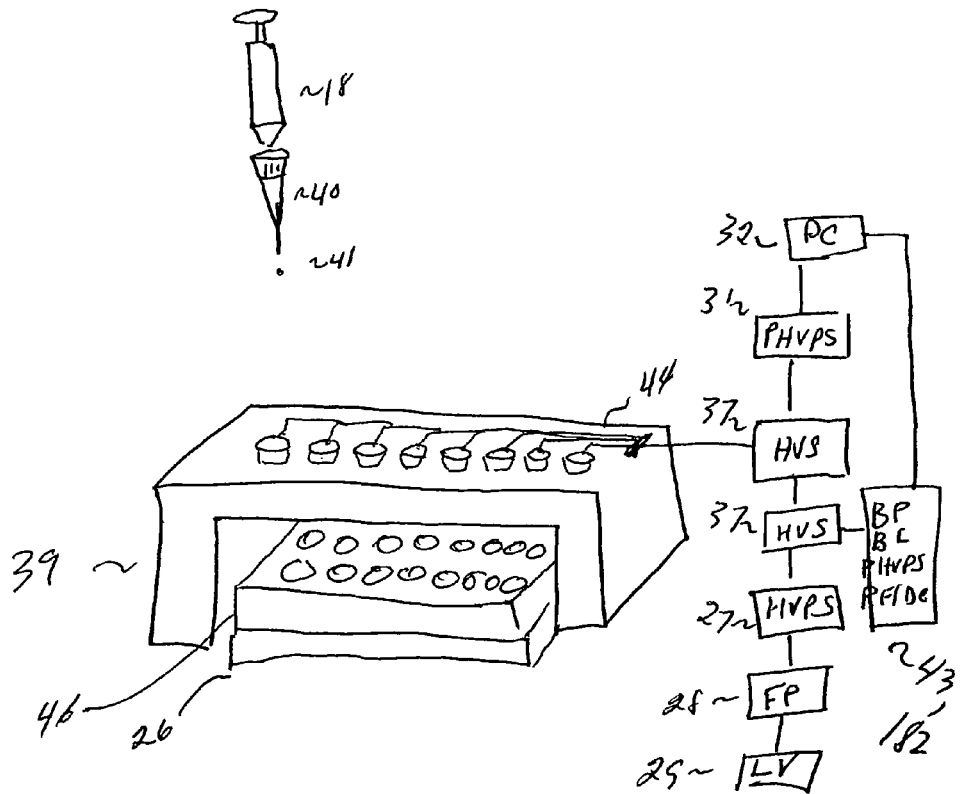
FIG. 18 IBF pipette and holder with DC/RF option.
Figure 19:
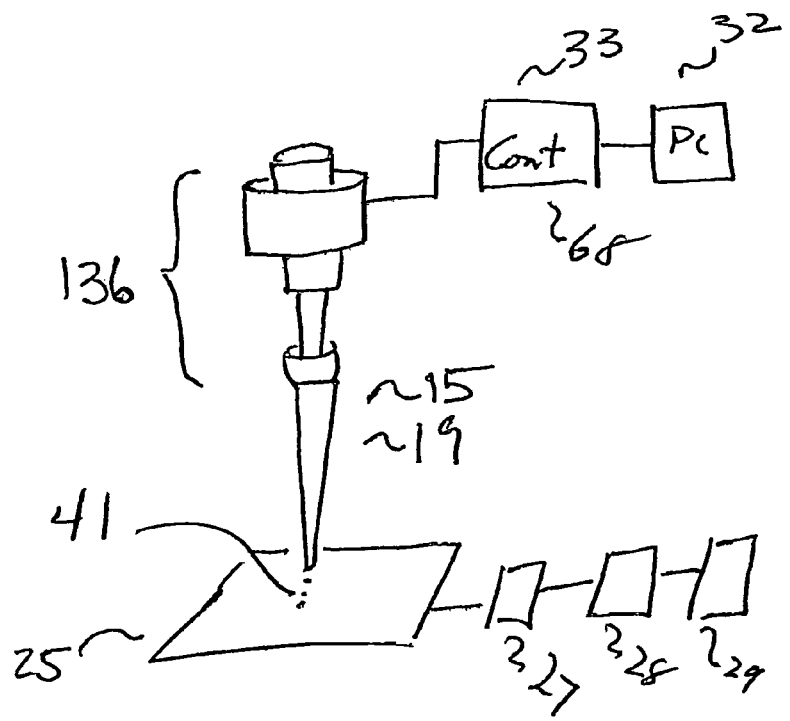
FIG. 19 IBF, air displacement nanoliter pipette embodiment.
Figure 23:
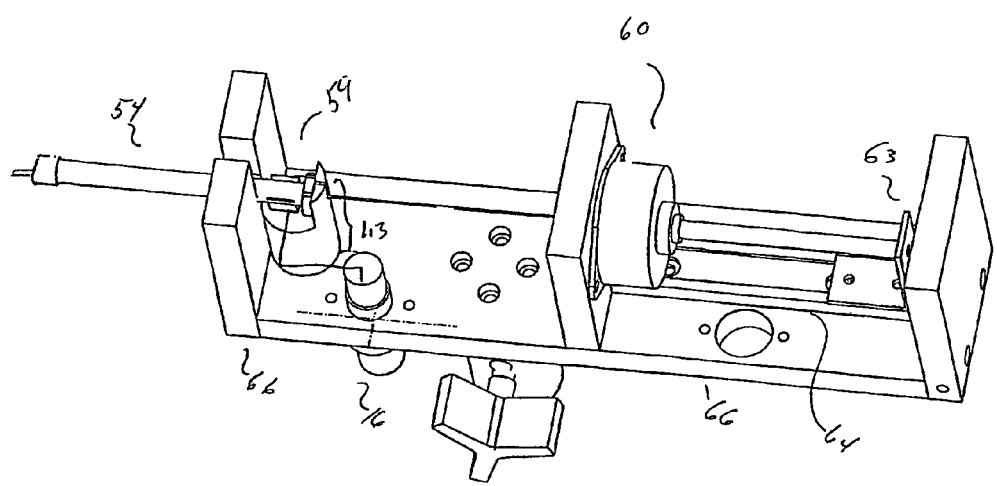
FIG. 23 IBF nanoliter digital syringe.
Figure 24:
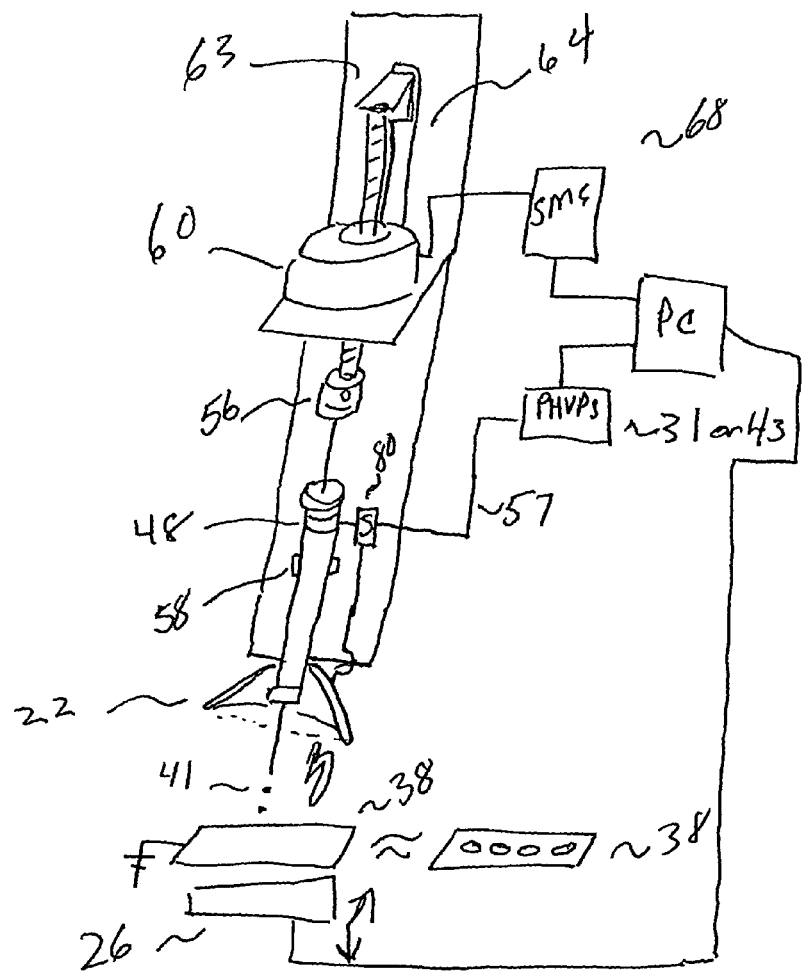
FIG. 24 IBF digital syringe with electric field focusing device.
Figure 25:
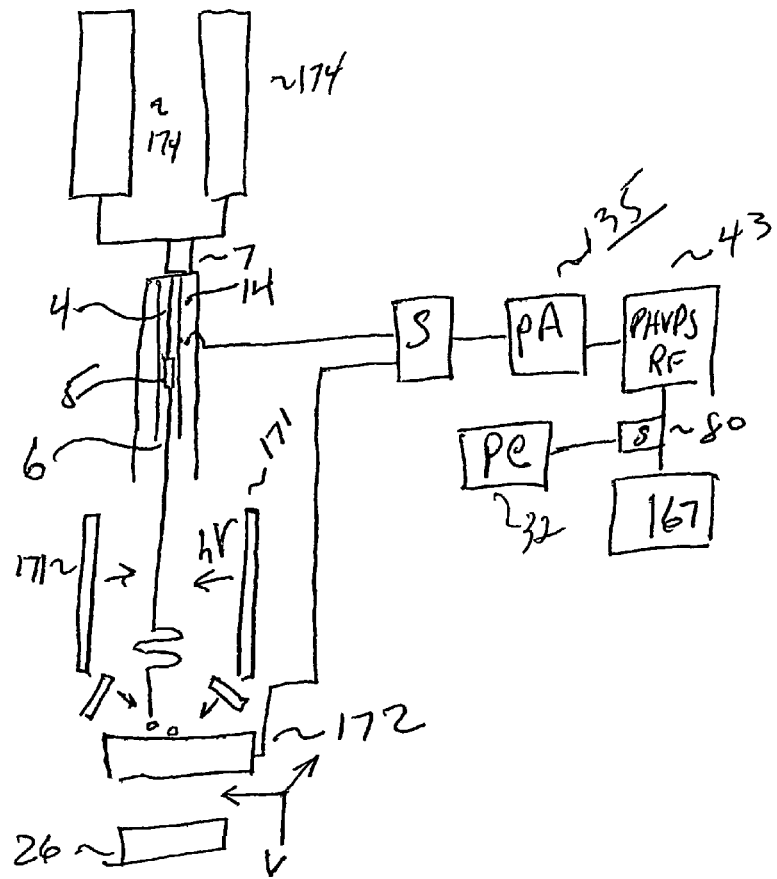
FIG. 25 Charged polymer manufacturing device.
Figure 26:
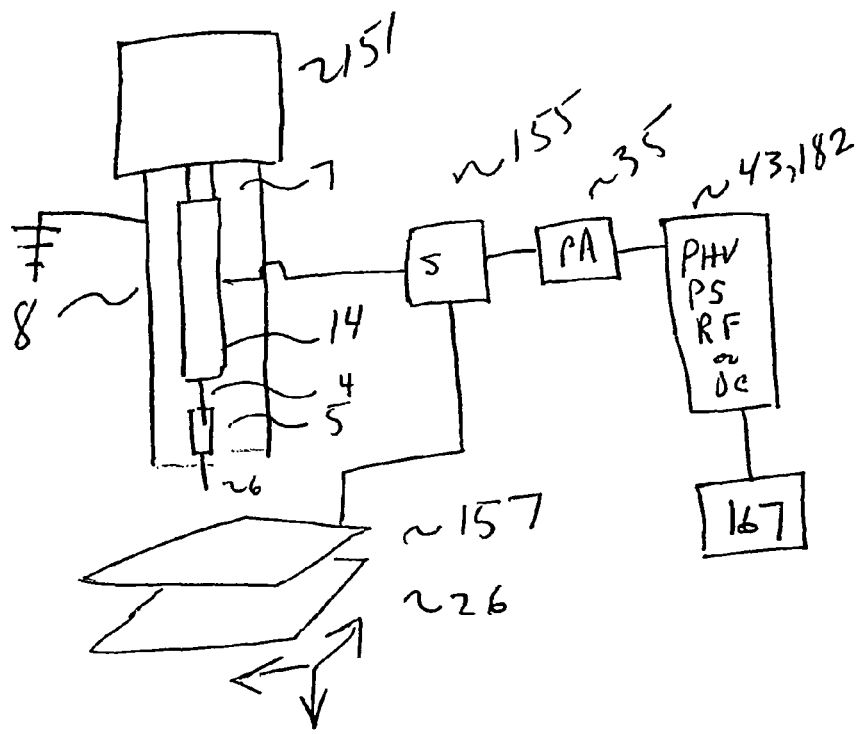
FIG. 26 IBF parallel LC
FIG. 27 IBF dispenser with inductor options and measuring devices.
Figure 28:
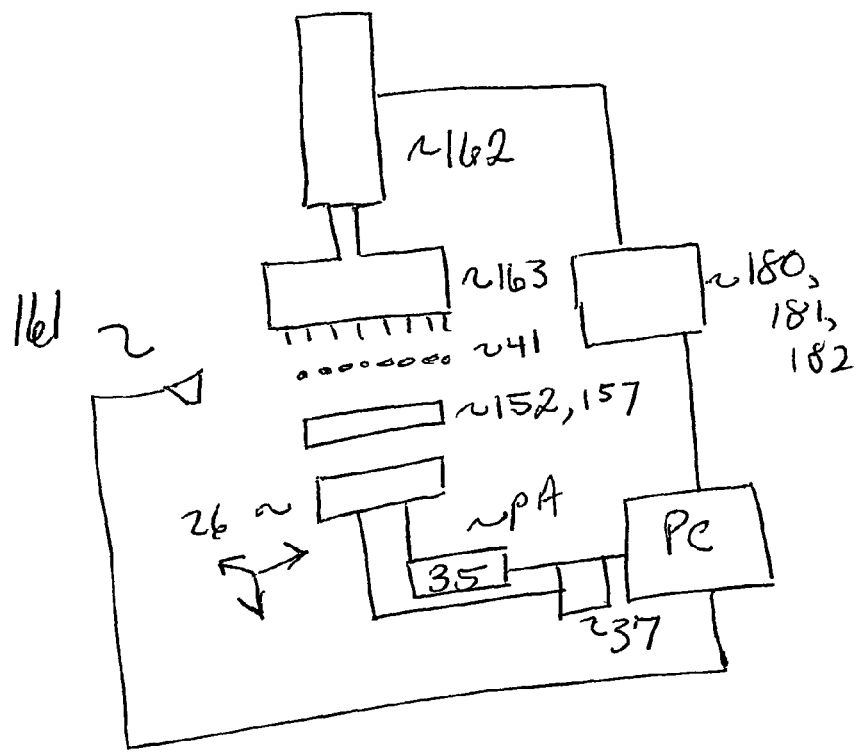
FIG. 28 IBF ULPC dispenser.
Figure 32A:
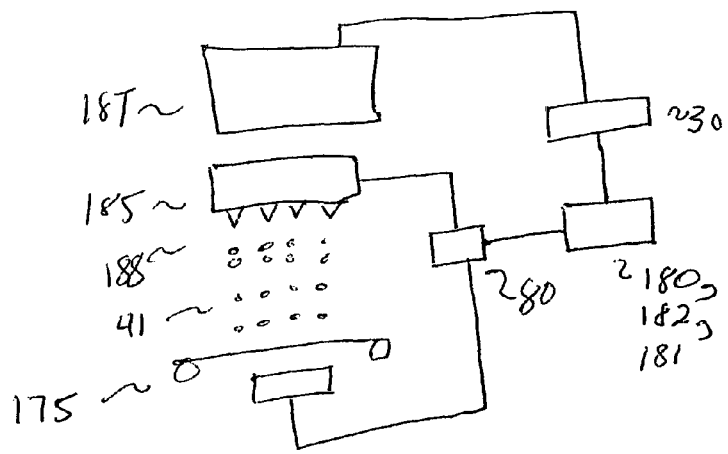
FIG. 32 IBF Douglas Array Tape, Nanoscreen, Roche polypipettor dispenser.
Figure 32B:
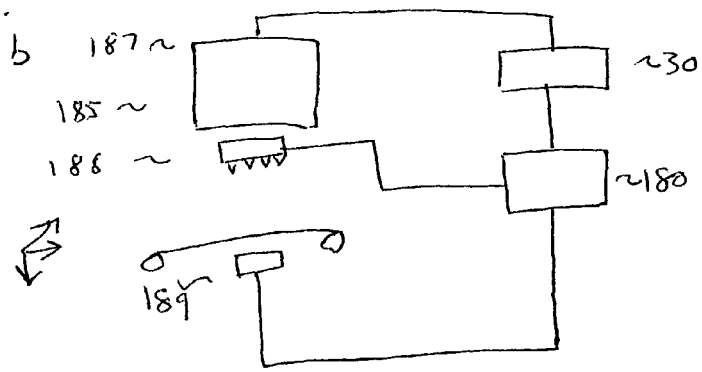
Figure 33A:
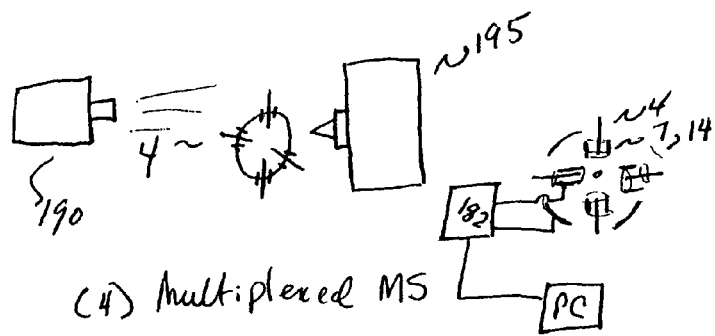
FIG. 33 IBF pipette DART interface.
Figure 33B:
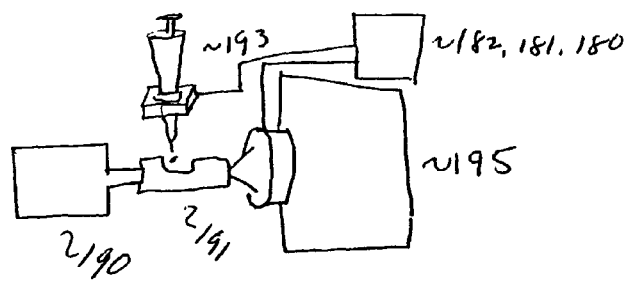
Figure 33C:
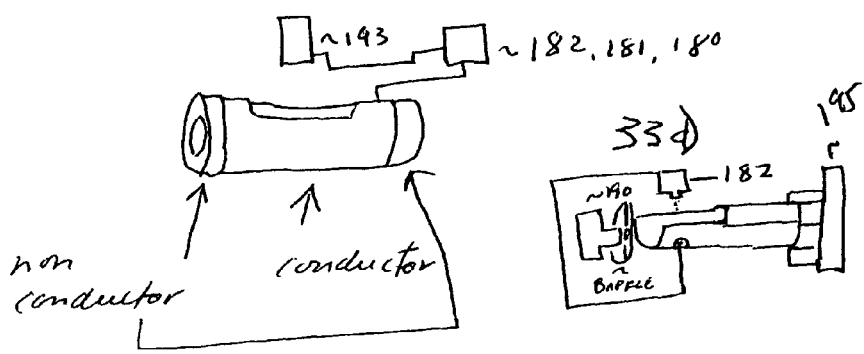
Figure 37:
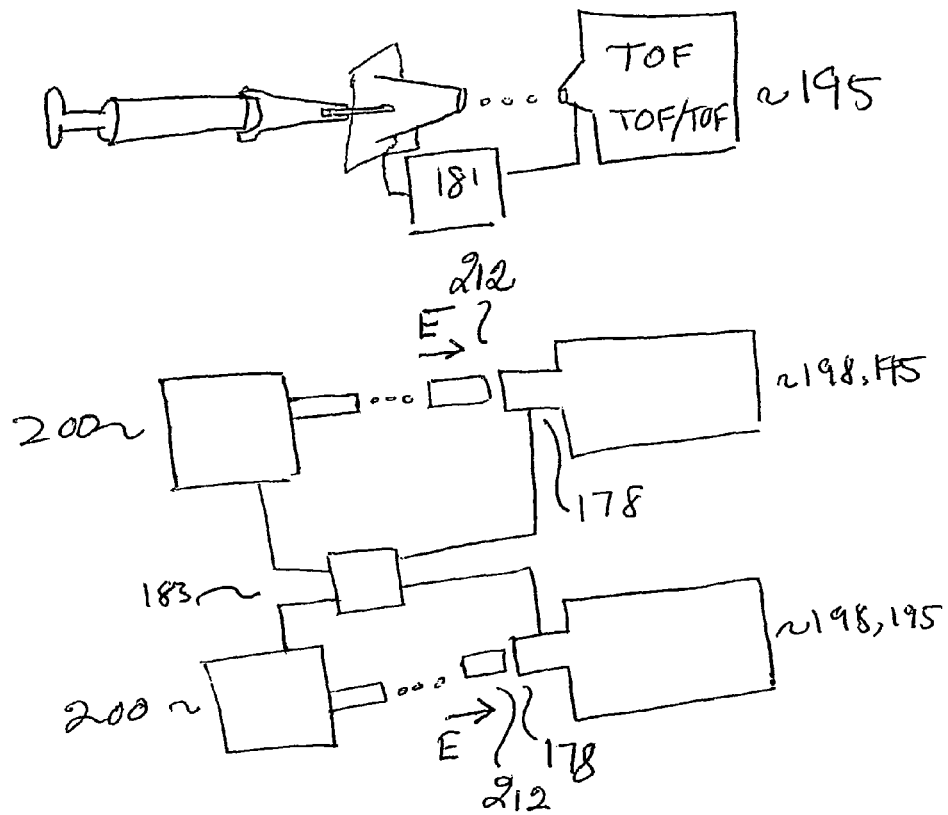
FIG. 37 IBF DART, ICP/MS, ICP/AES syringe, pipetter sample intro devices.
Figure 38:
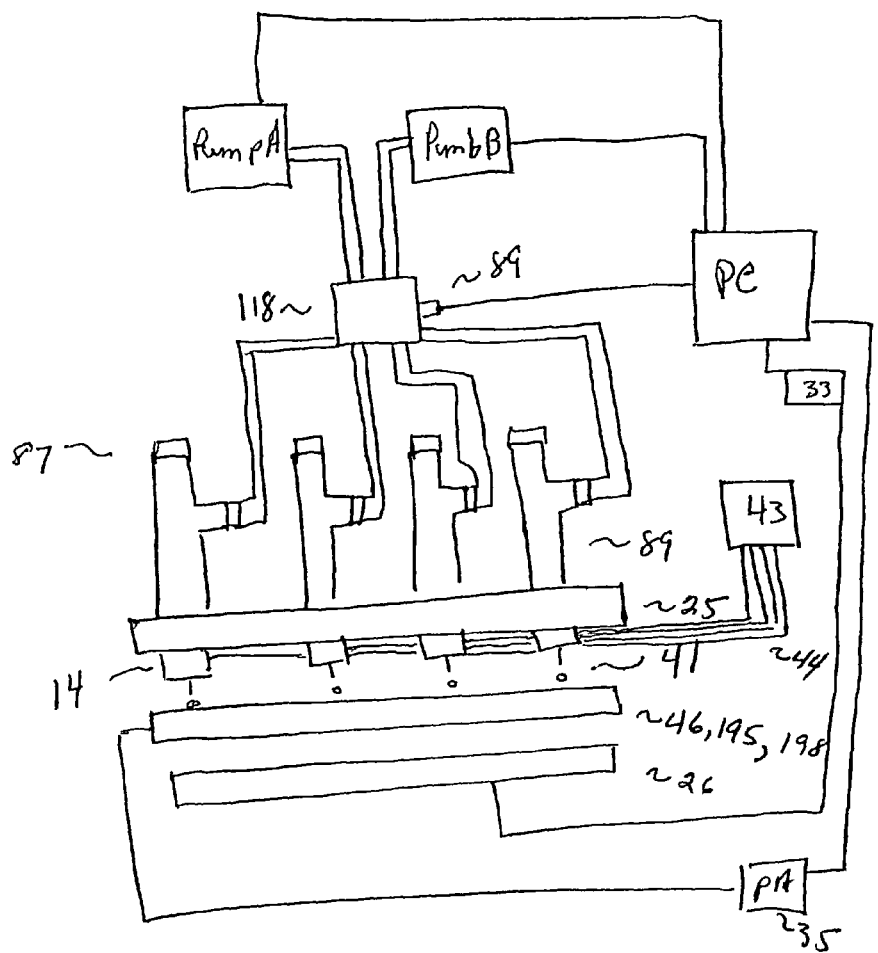
FIG. 38 IBF 4 channel MALDI.
Figure 39:
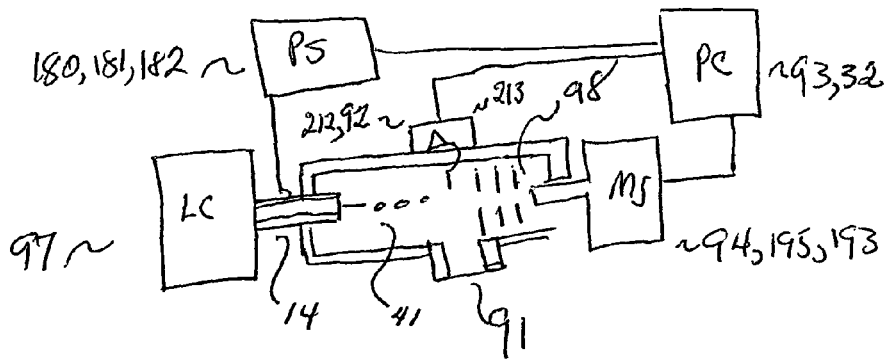
FIG. 39 IBF discrete drop sample intro device.
Figure 43:
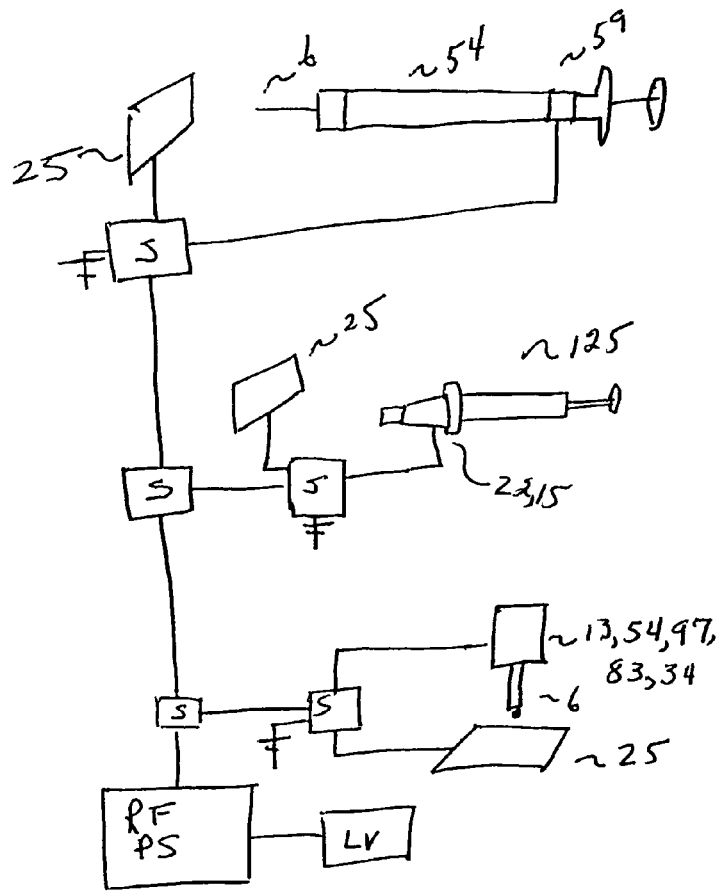
FIG. 43 IBF RF, DC or RF/DC syringe, pipette, pump composite device.
Figure 45:
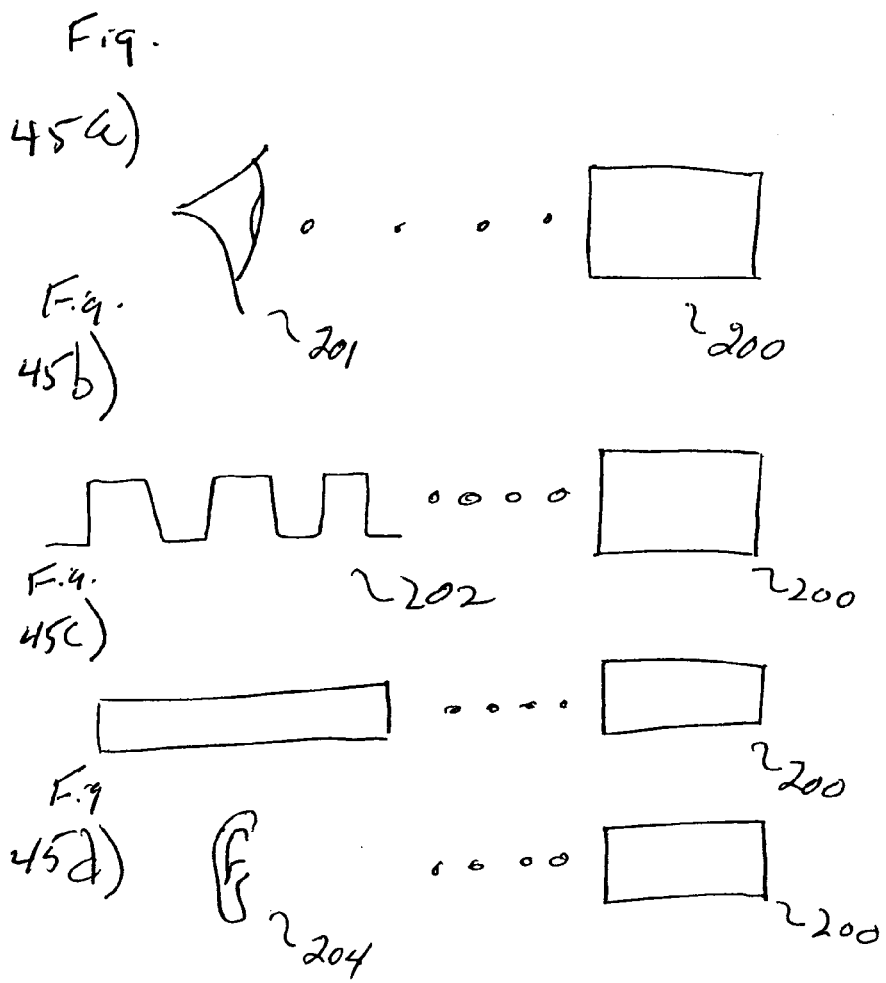
FIG. 45 nL human dispenser.
Figure 46:
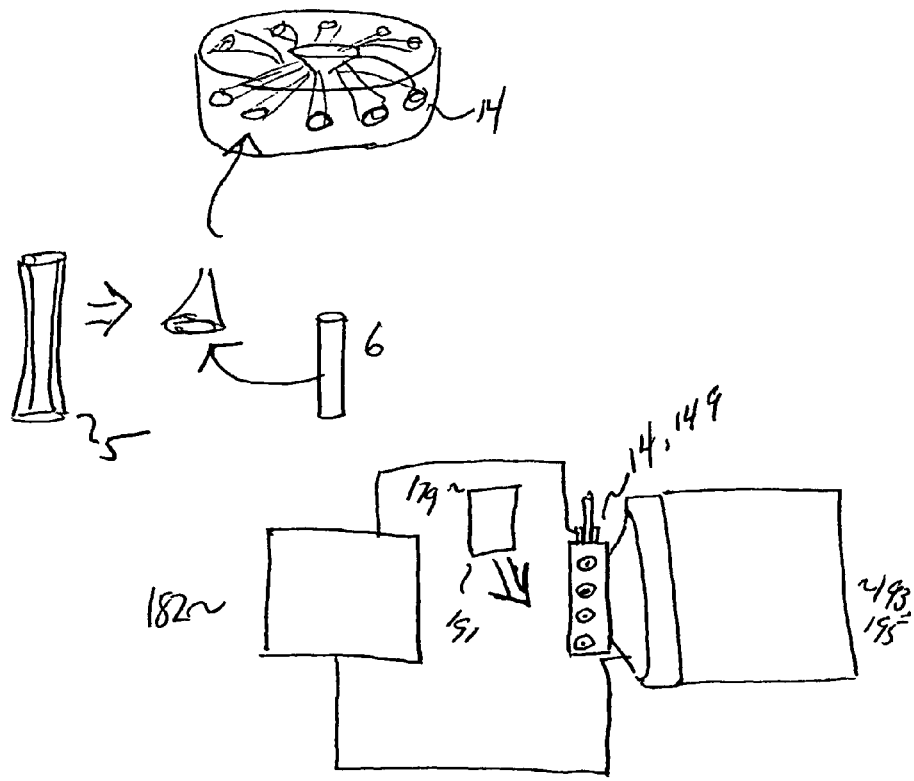
FIG. 46 n channel union.
Figure 47:
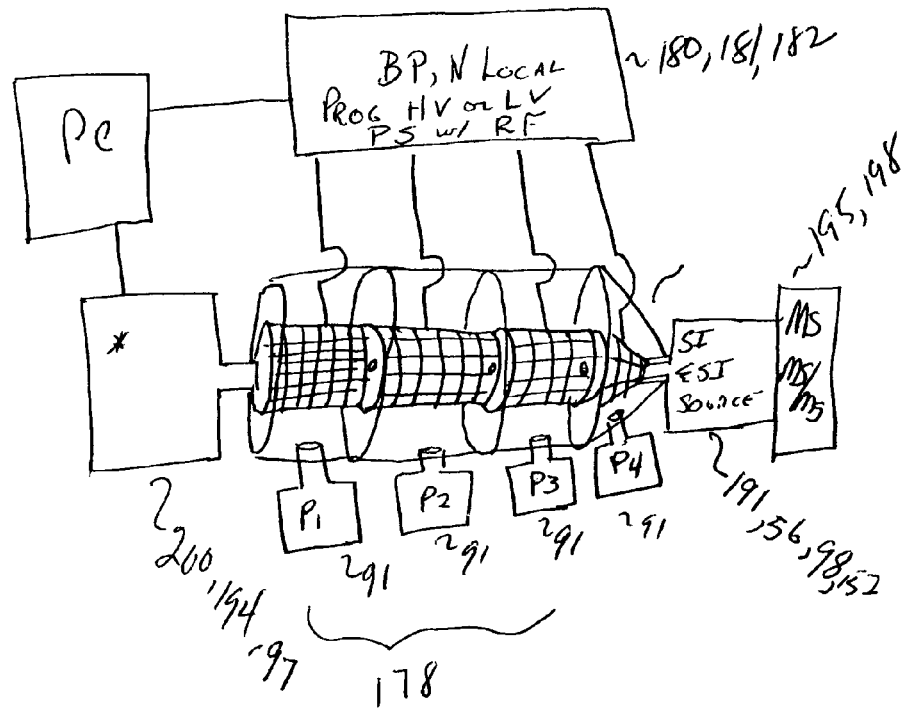
FIG. 47 IBF Accelerating denuder.
Figure 48:
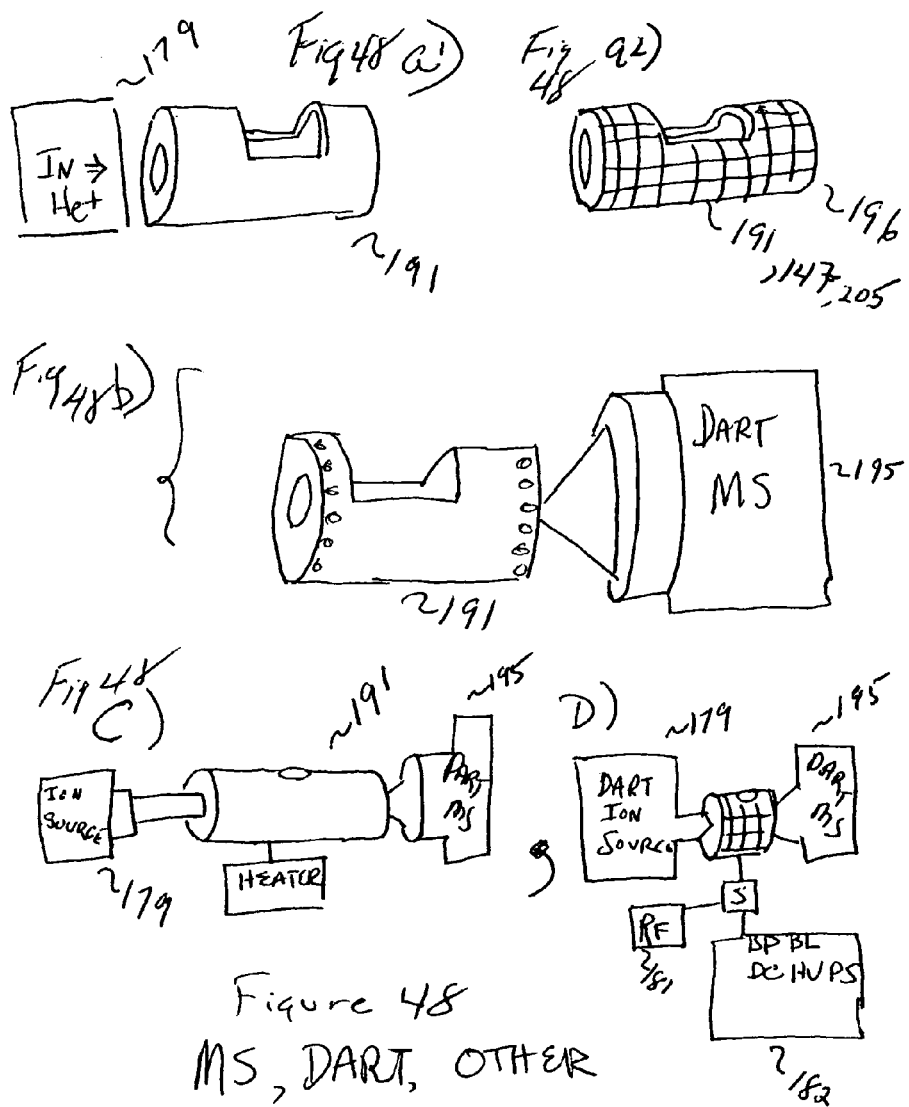
FIG. 48 IBF DART interfaces.
Figure 49:
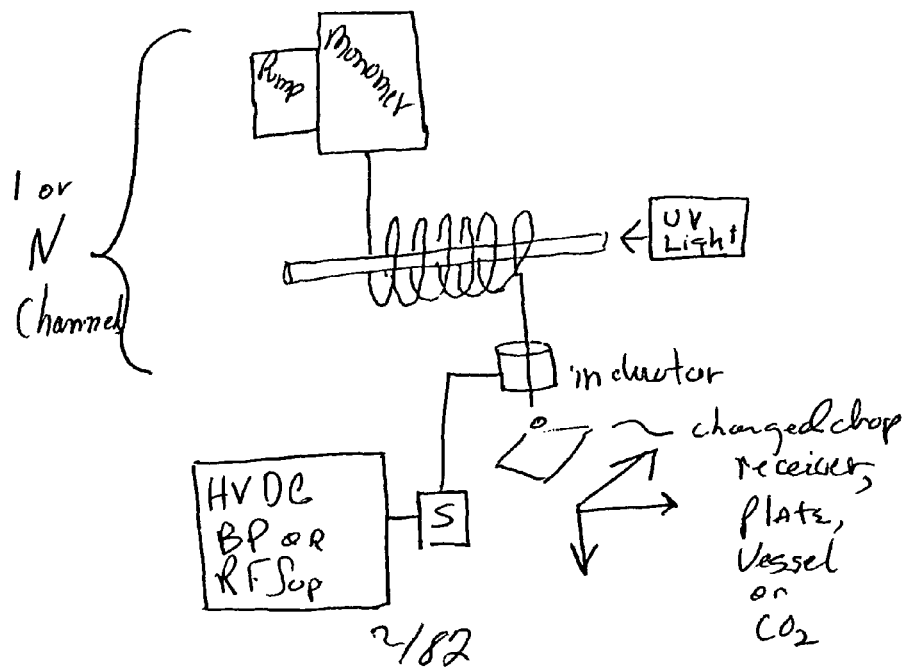
FIG. 49 IBF Charged polymer, liquid or f manufacturing device.
Figure 50:
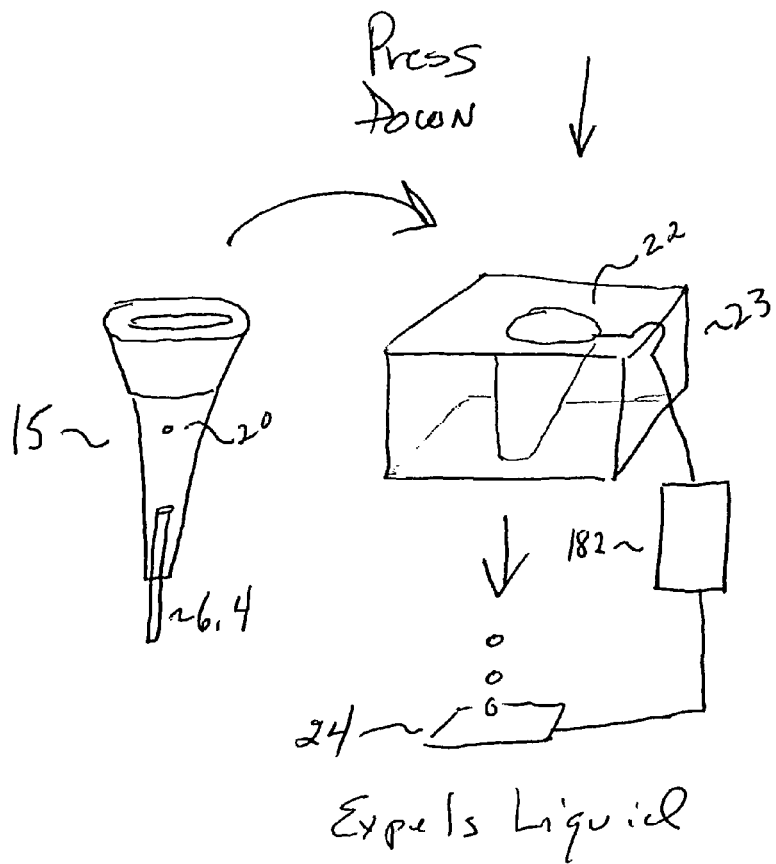
FIG. 50 Self healing nL pipette tip.
Figure 51:
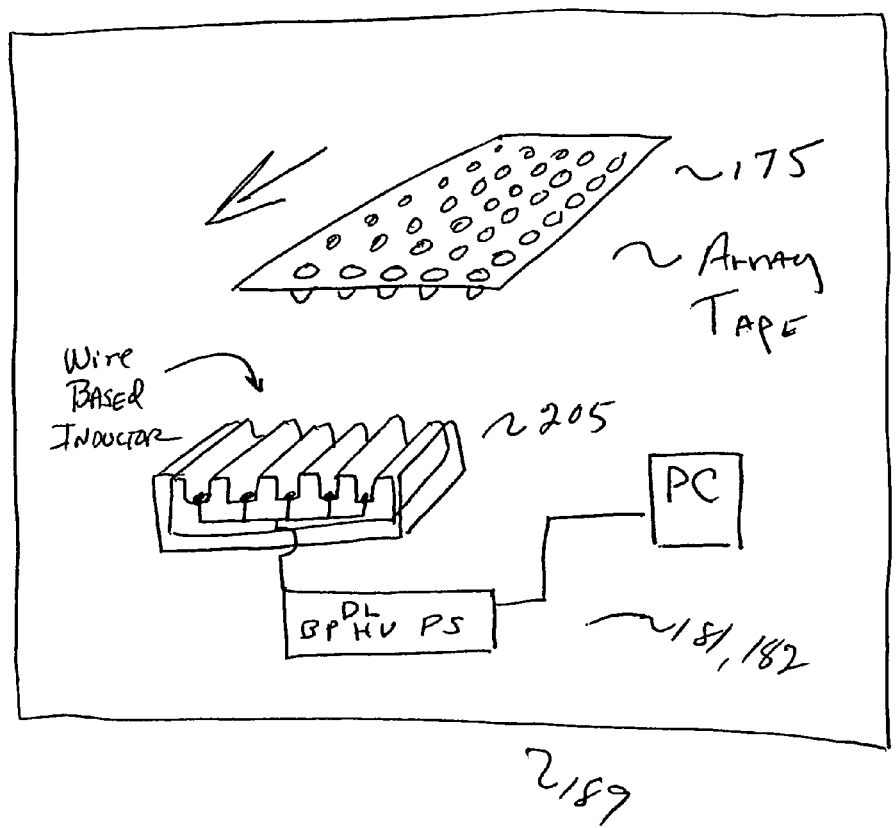
FIG. 51 n channel IBF Array tape charger and array tape.
Figure 55:
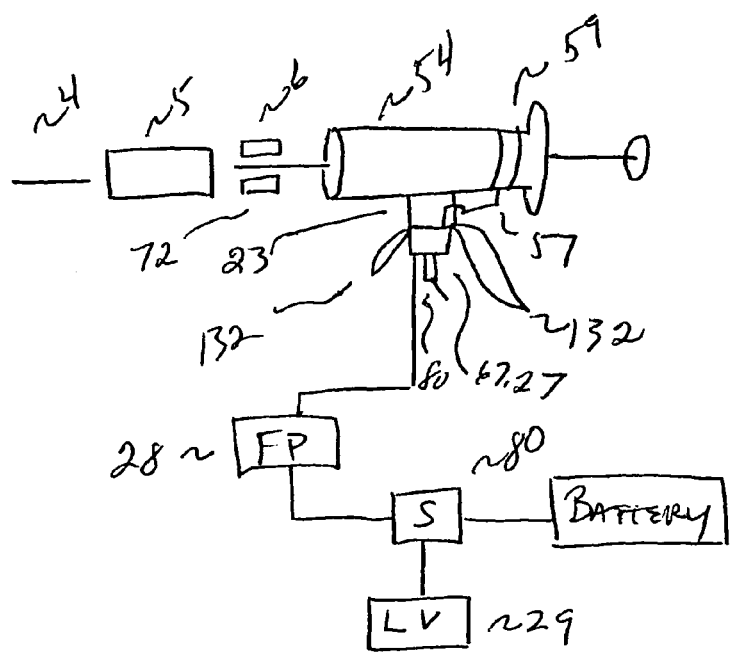
FIG. 55 Handheld LV or battery powered nanoliter IBF syringe.

Femtoliter to milliliter volumes of the same or different liquids are electrokinetically dispensed, treated, introduced or transformed or alternatively using a hybrid energy approach such volumes of liquid are dispensed, treated, introduced using electrokinetic and other energy sources such as mechanical pumps, peristaltic pumps, piezoelectric driven pumps, composite ultrasonic and thermal driven pumps, siphons, pistons, gravity or other manual energy sources such as plungers and other energy sources in a high parallel manner to various effects using a simple apparatus as per FIG. 1.

In this embodiment, a standard one microliter syringe is connected using an alligator clip or equivalent via the non-conducting glass barrel to a current limited, high voltage power supply that is connected to a source of power and that has an on off switch. The plunger is manually depressed and a bead of liquid is grown on the tip of some nanoliter volume. Whereupon turning the switch on to charge the liquid and upon placing a grounded human finger within approximately 1 cm of the drop, the drop launches or flys to the grounded human target thereby dispensing the liquid, liquid drug or other liquid to a human target without touching the human. Similar approaches work for food, plants, animals and other grounded targets.

In another embodiment, tubing connected to a standard syringe pump flows to a PEEK union which has a piece of PTFE coated fused silica capillary placed at the dispensing end of the union and to which a grounded metal plate is connected. Directly below which is a conducting plate of same geometry which itself is connected to a line source of energy (e.g. 120 or 240 v), a high voltage power supply and switch and upon which a grooved piece of dry ice 1 cm thick is placed. As the syringe pump is turn on and as it feed liquid to the capillary, a drop grows on the tip of the capillary whereupon turning on the high voltage power supply simultaneous charges the liquid and attracts and drops it to the dry ice. Upon turning off the pump and the high voltage power supply, the now frozen spherical drop being charged can be literally aspirated or picked up by a charged, cooled metal rod or a charged, cooled non-conductor just a charged comb can pick up small pieces of paper.

In another embodiment, 8 LC columns of any type are connected to high pressure LC pump via a manifold and tubing. The LC columns are individually injected via either capillary action or pneumatic techniques prior to connection to the manifold with sample. The eight columns are placed into a threaded ground metal plate using PEEK unions and to the manifold where the columns are separated by 9 mm. Below this is another conducting plate of approximately 25 cm×m10 cm which is placed on a robotic stage that can move in one direction. The upper conductive plate holding the LC columns is held by non-conductors like an acrylic plastic that also has a one direction of robotic movement (e.g., vertically); such that, it can change the separation between the ends of the LC columns and the lower plate. The lower plate is also connected to a programmable bipolar, current controlled and current measuring high voltage power supply which is connected to electronics that drive the power supply and which are connected to a microprocessor that drives the controlling circuitry which can be programmed form download C++ programs using and C++ function or series of C++ functions to change the voltage applied to the charging plate as any function of time.

As such, with the injected LC columns in the manifold, once the LC pump is turned on, and parallel LC ensues, the applied potential to the charge plate can be taken to some voltage such as +2.5 kV for 4.0 sec. and then square pulsed to +3.0 kV for 0.9 sec whereupon the voltage is reset to it's original value or +2.5 kV noting that the upper plate is at ground potential. As each program is executed, the LC columns placed a few mm above the charging plate is moved horizontally by 2 mm placing such drops in a temporally aligned and spatial tight row for applications including, such as, a MALDI target production for subsequent MS analysis by MALDI TOF MS for disease diagnosis, biomarker identification, polymer analysis, surface analysis or other applications.

In another embodiment of this technology a piece 20 cm piece of fused silica is placed into a liquid which contains a mixture of fluorescent chemicals, optionally liquids containing quantum dots based chemicals or other chemical species effecting a siphon. The tube of diameter 20 microns is attached to a charging plate and that to high voltage power supply and held above a grounded metal plate that rides on a robotic stage upon which targets such as pills, labels, food, identification materials and other targets are placed. When such targets are beneath the dispensing tip, the HV supply is energized dropping the liquid onto the grounded target for later identification or other purposes. Optionally, such dispenser or dispensers can be taken to high voltage (e.g., 15 kV) effecting a spray or a coating for a variety of purposes. Noting that as the liquid is not in touch with conductors, there can be no adverse electrochemistry, i.e. faradaic processes.

Another embodiment of the device is as a motorized syringe which has a plunger connected to a motor that drivers the former and with other accoutrements which can grow small drops on a tip which can be disposable and from which drops can be subsequently launched without touch or with touch drops to targets. Such a syringe is held in a plastic enclosure that contains other options including: a light to see the liquid, a laser pointer with focus for placing spots of known dimensions on targets for subsequent analysis by the video camera or jpgs resulting from vision analysis software output, a lens system to manually see the liquid and to read the scale, microswitches to display/select functionality via an IR remote or direct connect line to the base instrument, an LCD panel to display the volume or plunger locations or both, an LCD display to present syringe status and options, and optional rechargeable batteries on board and a power cord. This embodiment can also have an optional charge base made optionally or either non conductors such that charged drops expressed on the disposable tips can be literally flown to the charged grounded target non-conducting targets in a manner similar to how water drops are attracted to charged tube based TV or computer monitors.

Another embodiment of the device is a charged station where standard Hamilton (e.g., a Hamilton 701RNFS 10 uL syringe with the fused silica tip cut to 4.0 cm or with an alternate fused silica tip coated with PTFE) or other microliter syringes or containers containing liquids (e.g. 150 u capillaries with 146 u fiber optic plungers) can be placed onto conducting cradles. Such cradles are covered by non-conducting lids. Whereupon turning on an inexpensive, current limited the high voltage power supply connected to the cradles that hold the syringes or containers that contain liquids, charge the liquids therein. Subsequently, upon turning off the power supply, the devices can be removed by a gloved or non-gloved but not grounded human. Where upon manually expressing a drop to the tip of the syringe, and lowering it to a grounded surface, the drop flies to the grounded surface or target. This action can be repeated as long as the liquid remains charged.

In another embodiment manually aspirating a liquid into a Hamilton (Reno, Nev.) 701RNFS 10 uL syringe with the fused silica tip cut to 4.0 cm or with an alternate fused silica tip of the same dimensions coated with PTFE that is handheld by a non-grounded individual or by one wearing non-conducting gloves or alternately can be placed in a non-conducting mount like Panavise, is directly connected to the non-conducting body of the syringe via alligator or via an insulated HV shielded wire to the Teflon cap such that the conducting wires are not exposed, is connected to a Model No. 750 120 VAC-7.5 kV high voltage power supply from the Electronic Goldmine, which is connected to an autotransformer (e.g., Staco Energy Products, Model No. 3pn1010) which is connected to normal 120 v line voltage.

With the liquid in the syringe and manually expressing approximately 200 nL, and taking the device to 50 percent full power using the autotransformer, an d placing a target to 1.0 cm of the drop, and then rapidly turning the dial of the autotransformer to 75 percent full power the drop flies to the target, e.g., a grounded human finger.

In a related version with the same device, the plunger is manually depressed continuously as the autotransformer is at 100% full scale and a fine spray results on the target.

In a related version of the a similar device modified to have a coaxial non-conducting cylindrical shield extend over the end of the syringe barrel, and up to the end of the drops location, it is found upon depressing the plunger of an energized system that the spray is not created, but rather a drop remains for subsequent launching to a grounded target upon energizing same and pointing it to close to (e.g., a few cm) to ground.

In another embodiment of the device a twenty-four channel peristaltic pump (Idexcorp., Chicago Ill.) has its 24 lines brought to 24 PEEK unions and fitted with PEEK tubing such that standard 360 micron fused silica tubing of 150 micron ID can be joined thereto. This array is placed into a conducting plate with three lines of eight holes each row separated by 9 mm as per standard microtiter plate geometry with the tips of the capillaries being held on pipette tips, Plastibrand of Germany, 100 uL, above the ground plate by approximately 6 mm with a plate to plate distance of approximately 3.5 cm. The charge plate being connected to a AHV system 200 watt power supply and the ground plate being connected to that device's electrical ground. The charging plate is connected to non-conductors connect it to a z axis robotic system and the ground plate being connected to a z axis robotic with each plate being 10 cm×25 cm×1 mm. Upon the ground plate, a microtiter plate is placed and secured by plastic chuck, Upon the initiation of the primed pump, the microtiter plate is moved under the 24 channels and at the appropriate time (e.g., 1, 2, 5 10, 20 seconds, as selected), the HV supply is energized, as the current is measured dropping the 24 drops into the microtiter plate. This is repeated two more times, and in seconds a 96 microtiter plates has had liquids placed into it without touching the container.

In yet another embodiment of this device that is identical to the immediately preceding example except that each line of the peristaltic pump is has a unique liquid or in another identical version of the same device using a 96 channel peristaltic pumping 96 different liquids where one dispense cycle can place 96 liquids into one microtiter plate with great rapidity.

In yet another embodiment of this class of devices, any glass vial with a septum lid containing a liquid can be charged by placement into a conducting or a non-conducting holder that is connected directly to an AI-IV system 100 watt programmable DC power supply. A tube (e.g., od 360×id 100 u fused silica) is placed into the liquid and out of the top of the vessel through a septa with an optional vent. The tube further goes into a stylus that can be handheld. With siphon flow initiated, the I-IV source can be turned on resulting in a extremely fine spray in the pL/sec regime that results from the when the tip is a cm or so from ground. Such sprays can be placed on paper placed on electronic ground. Alternatively, the same device can be employed to dispense liquids onto non-conductors when it is they that are the charged targets and when they are charged in a siphon or pump based system.

In an identical embodiment of the preceding example, the dispensing tube goes to a manifold with eight outputs that can place the same liquid in eight locales concurrently.

In one further embodiment the device is employed to send charged liquids into scientific instruments directly from LC columns without creating or with creating a spray where in the former mode, MS sensitivities are greatly increased as a great fraction of the analytical sample reaches the instrument; such as a mass spectrometer.

In one further embodiment, the dispensing is from an IBF source to a Nanostream syringe array or array of capillaries into array tape made by Douglas Scientific on a DNA platform where any individual lumen can dispense N at a time or individually as the charge is measured coulombically.

All or anyone of these devices can be placed into a fume or environmental chamber or faraday cage or all three to affect a controlled environment.

DRAWING REFERENCE NUMERALS

1. Spark Holland needle tube assembly from a SP Alias liquid handler.
2. Up church PEEK nano union.
3. Fused silica tubing in FEP sleeve.
4. 360/150 od/id fused silica or other tubing of any OD/ID unpacked/packed w/ stops, filters, SPE, Immunoassay, LC or other media.
5. Quartz GC compression union.
6. 360/50 id/od fused silica, Teflon coated, other tubing, of OD/ID un or packed:stops, filters, SPE, Immunoassay, LC or other media.
7. Conducting union.
8. anti EMI/RFI shield version 1.
9. anti EMI/RFI shield version 2.
10. anti EMI/RFI shield showing in/out gas lines.
11. Complete device with circuit and gas connectors and gas & vacuum pump.
12. Bottom view.
13. Spark Holland Alias Liquid handling device with inductor above 384 position MALDI plate.
14. The inductor.
15. Pipette tip modified for IBF dispensing
16. Analogue HV circuit
17. HV protection and current measuring circuitry.
18. Bottom view of air displacement pipette.
19 Pipette tip
20. Hole in tip.
21. Compression fit fused silica.
22. Conical metal conducting cone, an inductor.
23. holder.
24. receiving device, a cup or equivalent.
25. conducting surface.
26. robotic x, y, z, movement device.
27. high voltage power supply, low current.
28. foot pedal switch or rheostat.
29. Line voltage, 120 v.
30. high voltage protected current measuring device.
31. programmable high voltage power supply.
32. PC
33. Robotic controller.
34. 8 channel air displacement pipette.
35. Picoammeter or electrometer with HV protection circuit.
36. Low current Keithley scanned card system, 7053.
37. high voltage switch.
38. Conducting receivers.
39. IBF pipette holding device
40. IBF pipette tips.
41. Drops of liquid.
42. HV protection devices (e.g., HV resistor).
43. Bipolar programmable HVPS with both DC and RF supplies.
44. HV shield wires.
45. HV shield connector.
46. MALDI plate.
47. Pipette tip puncture stand.
48. IBF charging device.
49. Conductive coating of any kind.
50. Color coded conical sleeve and holder.
51. Conductive tip.
52. Non-conductive coating.
53. Gaussian surfaces w/ cut tip of any lengths and coatings w/ precise radii w/ different tip cut shape or coating of any geometry or other tubing of any OD/ID unpacked/packed w/ stops, filters, SPE, Immunoassay, LC or other media.
54. 701 Hamilton Syringe or equivalent.
55. micrometer.
56. device coupler.
57. HV lead.
58. Syringe holding base.
59. HV attachment.
60. Stepper motor.
61. HV fitting input, Alden
62. Positioning screw tightener.
63. Aluminum L bracket connector.
64. Aluminum track and riding mechanism.
65. High precision screw
66. Digital syringe holding base.
67. Analogue HVPS
68. Digital stepper motor controller.
69. IBF digital nanoliter syringe.
70. Programmable HVPS
71. Bipolar analogue of HVPS.
72. Heat shrinkable polymeric tubing.
73. Glass tubing.
74. Tubing with deactivated surfaces.
75. Surface activated tubing.
76. wire coil of wire
77. coil holder
78. connectors.
79. Super glue in a tube.
80. Switch
81. Screwbody with shielded HV connector.
82. PHVPA with optional RF PS.
83. IBF nL syringe.
84. Tube, nonconducting.
85. IBF inductor.
86. PEEK T
87. Injection port.
88. Polymeric or other isolation valves.
89. Flow sensor.
90. Charged porous inductor.
91. Vacuum pump.
92. Resistor or IR heaters
93. Data system as in mass spectrometry.
94. Mass spectrometer.
95. Cylindrical housing.
96. Solenoid controller with feed throughs.
97. LC influent or influent from another device, e.g., a pump.
98. Ion optics with skimmers and offices.
99. Human thumb or part.
100. Liquid being pulled into a cone jet.
101. Liquid solvated clusters or drops.
102. Flexible charge tube.
103. Optional variable orifice.
104. HV attachment device.
105. Expansion chamber.

106. Variable inlet or valve.
107. Low current ultra light HVPS
108. Semi-pernable membrane.
109. Seals.
110. High surface are polymeric material, inductors.
111. Color coded fused silica for inductor.
112. Conductively coated fused silica for inductor.
113. EVCL, exact volume cut line or a scale.
114. Coil inductor.
115. Coated syringe connector.
116. 3 way HV switch.
117. Shortened metal tip covered with a Teflon or related coating to allow for compression fitting.
118. 8 fold, a manifold.
119. Induction, conductive leads.
120. Slightly tapered conical hole.
121. Teflon washer/sleeve.
123. Radio frequency power supply.
124. 4 way switch.
125. nanoliter pipette
126. nanoliter syringe
127. a syringe pump
128. 8 coupled throughput manifold.
129. Chip based manifold.
130. Keithely 7022k card system.
131. HV leads.
132. Aluminum frame.
133. HV connector.
134. HV connector cover
135. Bat toggle switch.
136 Upchurch, Y connector & Bat Toggle Switch.
136. Air displacement pipette motor.
137. Holder, 30 mom.
138. Alignment rail.
139. HV connectors
140. 8 fold compression union.
141 Ground plate
142. Microfluidic chip.
143. 53A assembly.
144. Equal path length gaussian surfaces, capillaries or channels.
145. Metal or other inductor.
146. PEEK Tubing.
147. Conductive coating.
148. Wire or other coil.
149. inductor.
150. 150 micron id or other fiber optic coupler, BD.
151. Fluidic devices of all types, gaussian surfaces, powered gaussian surfaces or chips or manifolds and the like.
152. Parallel fluidic devices of all types, gaussian surfaces, powered gaussian surfaces or chips or manifolds and the like.
153. Radio frequency power supply.
154. Moving fluidic targets, like microtiter or MALDI plates, etc.
155. Fast, millisecond or microsecond low or high voltage relay switch or switches.
156. LC column/s or any other type of analytical chemistry columns.
157. Targets of any type including but not limited to conducting, R coated conducting and other non-conducting matter like: MALID plates, microtiter plates, cups or vials of any kind, living matter, non-living matter, conductors of any kind and other targets like electrical components and the like.
158. peristaltic pump of any kind.
159. high pressure LC or any other type of pump.
160. Cylindrical conducting inductor with cone shaped energy focusing end.
161. Digital camera with pixel counting software for quantitating drops.
162. Programmable computer controlled high or ultra high pressure dual pump solvent progammable LC system.
163. Manifold of N fold, computer controlled potential with optional individually addressable IBF or other valves.
164. EMI/RF shielded 360/150 od/id fused silica or other tubing of any OD/ID unpacked/packed w/ stops, filters, SPE, Immunoassay,
LC column packing or other media.
165. Liquid MALDI matrix pump.
166. Liquid reservoir with an optional pump.
167. Nanoliter, LLC designed microprocessor or HV and/or switch controller.
168. Liquid chromatograph with solvent programming capabilities, optionally, UPLC.
169. PEEK T or optionally a PEEK cross.
170. N channel, e.g., 8 valve, automatic or manually operated.
171. ultraviolet lights.
172. Movable charged polymer collection area.
173. Monomers with polymerizing agents.
174. Monomer and reagent liquid feeding pumps.

* * *
New Since 2005
* * *

175. Array tape,
176. Nanoscreen parallel dispensing syringe system/s.
177. Accelerator
178. Degassing accellerator
179. DART ion transmitter, liquid deposit device or DESI devices.
180. Programmable, Bilocal, Bipolar DC HV PS.
181. Programmable, Bilocal, Bipolar DC HV PS with programmable RF option.
182. Programmable, Bilocal, Bipolar DC HV PS with programmable RF option and quad
183. High voltage or normal relay switches.
184. N channel capillary array with 384, N channel cylindrical inductors.
185. 384, N channel capillary array, 384, N channel cylindrical inductors shield.
186. Manual pipette or digital pipette.
187. Roche 384 polypipettor
188. Inductive array Gaussian surface, capillary, pipette, manifold, pumps outlet ho
189. Douglas Scientific roll and Z, y robotic device with form fitting pipette top inductor and grooved for fitting bottom inductor.
190. DART ion source.
191. DART interface.
192. Digital syringe.
193. Digital or manual syringe.
194. Digital nL IBF pump.
195. DART TOF or other MS
196. Screen material for gas pump through.
197 HV resistors
198. ICP AES or ICP/MS
200 IBF nL, pL, uL, fl dispenser of any type.
201. eye
202. teeth
203. any human appendage.
204. human or other ear.
205. grooved, wired inductor
206 capillary array
207 cylinder array.

208 HV selector switch
209. Holed inductors.
210. User selectable IBF dispenser.
211. User selectable IBF dispensing and measuring device.

ABBREVIATIONS

Prog.=programmable
Bipol=bipolar
HV=high voltage
Comp=computer
pA=piocammeter
Elect. Electrometer
Rob Cont=robotic controller
HVPS=high voltage power supply
FP=foot pedal
LV=line voltage
HVS3=three position HV switch
Control=controller
AHVPS=analogue HVPS
PHVPS=programmable HVPS
PC=personal computer.
RF=radio frequency
RFHV=high voltage RF power supply.
N channel=1 or many channel device.
RFPS=radio frequency power supply
PS=power switch
EVCL=exact volume cut line.
ES=electrostatic
MTP=microtiter plate
PHVPS=programmable HVPS
7002k=Keithely 10 slot 7002 switch.
7058K=Keithely 7058 Scanner.
Ind=inductor
nLw=nanoliter syringe
FS=fused silica
GC=gas chromatography or gas chromatograph.
IBF=induction based fluidics
HVPCir=high voltage protection circuit
HVP CMD=high voltage current measuring device.
Lcur Scan Card 7053=low current scanner card system, Keithely 7053 or equivalent.
PPP=programmable piston pump.
HVCoolSYS=negative or positive polarity HVPS, electrodes or conductive surfaces and polymeric inductors and AC, DC or battery based energy supply.
LC=liquid chromatography.
DS=data system, typically software and operating system and a computer and other typical accouterments.
MS=mass spectromter
VP=vacuum pump
Delta=heat
ZDU=zero dead volume, SDAFS=surface deactivated fused silica

What is claimed is:

1. An induction based fluidic apparatus for inductively transporting or dispensing materials which is a) useful for accurately transporting or dispensing one liquid or for accurately transporting or dispensing a plurality of the same or different liquids, in similar or different microliter to femtoliter volume ranges, and optionally, b) is useful for performing one or more other operations concurrently or sequentially on the same or different liquids including those eluting from capillaries, pipettes, syringes, syringe pumps, dispensers and pumps of all types, SPE columns, chips, HPLC, UPLC or other liquid handling and treatment devices or pumps and devices that align and couple matter flows and optionally provide energy to it for transport to mass spectrometers of any type or other scientific or other instruments energizing same with sample placement devices; and furthermore which, c) is useful for accurately and precisely in both volumetric and spatial terms delivering treated liquids or liquids, drugs, anesthetics, taggants, slurries or cells, dissolved cells, suspended cells, biological fluids, DNA/RNA samples, glues, whole blood, paint, lubricants, viscous liquids, tears, serum, semen, or suspended or other solids including nanoparticles to entities of all types including MALDI targets and microtiter plates, mass spectrometers and scientific instruments or all types, drugs or prescriptions, food, plants, animal and human subjects, packages or containers of all types, inanimate objects, and other objects either of a conductive, semi-conductive or non-conductive material, rapidly, without touching same, and d) which is useful for manufacturing of 2D and 3D components; such as charged functionalized solid entities or polymers or mixtures thereof, or non-charged polymers or pills, or wafers and or electronic or other components and e) which is useful for sample preparation for MALDI, tissue MALDI, and LC/MALDI, LC/ESI/MS and IMS variants and also for the characterization of bacteria by MALDI, SIMS, DART, DESI, LDI or other energy, target systems and which is also useful for desolvating fluids of all types and which is also useful for sample preparation and sample introduction and other testing related to medical diagnostics, disease and health biomarker testing via liquid processing to assess the condition of living or other systems which is comprised of:

a) a source or electric power;
b) at least one on/off switch;
c) a programmable digital bipolar electric HV power supply with each pole electrically connected to at least one fast HV relay switch;
d) HV flying leads electrically connected to said HV relay switch and electrically connected to at least one inductor and switchably to targets or ground;
e) a computer or microprocessor, which is programmed to select and control energy, polarity and application locale of power and which is connected to circuitry to select individually said at least one inductor and or said targets;
f) at least one gaussian surface located inside and enclosed by the said at least one inductor with a terminal end of said gaussian surface open and connected to at least one UPLC system, HPLC system, or dispensing system;
g) energy and actions of said at least one system are coordinated by said microprocessor or computer to apply and to coordinate said electrical energy to said at least one inductor or to said targets in coordination with said at least one UPLC system, HPLC system, or dispensing system to create one or a plurality of fluidic paths to allow for the creation drops, flows, or sprays;
h) at least one IR heater or resistance heater to further energize the said drops, flows, or sprays and wherein such energization is coordinated by said microprocessor or computer that likewise coordinates said droplet production;
i) where the at least one inductor through which said drops, flows or sprays are caused to move in the atmosphere are aligned and/or connected to at least one scientific instrument;
j) said at least one scientific instrument has a sample introduction robotic device to provide relative motion for sample introduction to and from the said UPLC system, HPLC system, or dispensing system, with said robotic device being controlled and coordinated by said microprocessor or said computer.

2. The apparatus of claim 1, where at least one non-conducting cylinder containing at least one embedded conducting cylinder is connected to the flying leads wherein at least one non-conducting gaussian surface, capillary, or LC column, is attached to a non-conducting fitting placed at the entry end of said non-conducting cylinder whose said gaussian surface is likewise non-conducting and that is connected to at least one compression fit union at the distal end of said surface and where said gaussian surface, and said cylinders have at least one through hole connecting to tubes and gas fixtures for the exit of at least one gas that can be thermally or otherwise pre-energized.

3. The apparatus of claim 1, where at least one IBF dispenser, and at least one LC column or other gaussian surface and an ESI ion source are coaxially aligned and connected at terminal ends to at least one tube, cylinder, or housing being coaxially aligned with the exit flow of said ESI ion source from said IBF dispenser being connected by at least one tube to at least one mass spectrometer analyzer compartment where the interior of said housing also contains at an entrance of said chamber a wire or filament and a ground plate connected to at least one regulated programmable DC power supply finally containing a cylinder connected to an ammeter or electrometer.

4. The apparatus of claim 1, where at least one dispenser or gaussian surface is located near the termini of at least one inductor equipped IBF dispenser wherein any adjacent energy source is co-located such that said dispenser is placed immediately in front of an ESI ion source, another mass spectrometer ion source or scientific instrument or MALDI, microtiter or other plates, or other receivers.

5. The apparatus of claim device of claim 1, wherein an IBF dispenser contains a gaussian surface, whose exit termini is coaxially near an electrically energized, and heated tube being placed immediately after said dispenser, LC column, capillary or any gaussian surface, with said arrangement located adjacent to a target, including but not limited to, an ESI ion source, another mass spectrometer ion source, a robotically movable MALDI, or microtiter plate targets where said arrangement of said dispenser and said target or targets is physically separated, and robotically movable and is open to the atmosphere, said device being encased in a enclosure.

6. The apparatus of claim 1, further comprised of N co-linear cylindrical chambers, each separated by an orifice, where each of said chambers is attached to at least one vacuum pump and where each chamber contains conical screens and conducting plates, each individually connected to DC power supplies whose DC potential is individually controlled by a programmable DC source that is bipolar and is connected to a programmable RF source of energy.

7. The apparatus of claim 1, further comprising an N channel dispenser comprised of a manifold with conducting surfaces on the end of each of N ports on said manifold electrically HV isolated from the other, with each port connected with N flying leads to a grounded, N Channel, N fast HV relay switches to a programmable bipolar HV power supply with a microprocessor or computer that is used to control polarity, energy, location, and timing of application of energy from said power supplies, to said dispenser and to said flying leads.

8. The apparatus of claim 1, further comprised of at least one bipolar programmable HV DC power supply directed by a microprocessor or a computer equipped with at least one fast HV relay switch connected at each pole to flying leads, connected to at least one non-conducting cylinder and one target where said inductor or said target can be energized in coordination with the complete UPLC, HPLC or other dispensing system and where said inductor contains liquid in said gaussian surface or said targets and can be brought to any programmed energy, polarity or locale by induction without touching the liquid with conductors, and where fluid exiting from a distal end or near said inductor touch the said inductor and said fluid is located by an output from at least one programmable energy source in said inductor.

9. The apparatus of claim 1, wherein at least one gaussian surface connected to a at least one programmable DC or RF power supply and at least one IBF dispenser is located off axis to the entrance of an ESI or other source which has an axially located source of programmable IR energy, whose actions are coordinated with at least one microprocessor or computer.

10. The apparatus of claim 1, where a grounded metal cylinder with a flange on each side of said cylinder is connected to or placed in front an ESI ion source and that optionally contains an inductor, LC capillary outlet or both, sealed at the inlet edge with fittings welded to a blank metal plate fitted to said cylinder.

11. The apparatus of claim 1, where electronic energy emanating from a wire or a filament connected to a regulated DC source of electrical energy, equipped with a lower energy or at ground, plate is set at a distance from said filament whose current is measured with an ammeter and whose body is enclosed and attached to a front or rear end of an ESI ion source.

12. The apparatus of claim 1, wherein least one non-conducting tube affixed to a flange with a through hole contains a shorter conducting tube or gaussian surface, an inductor, enclosed therein connected through which the flying leads are attached to said conducting tube and that contains at least one disk with at least one hole fixed a distance inside the distal end of said non-conducting cylinder.

13. The apparatus of claim 1, wherein one or a plurality of a programmable digital, bipolar, HV DC power supply, are connected to as many digital RF power supplies through circuitry, and at least one fast relay switch is connected to each pole of at least one said supply that is controlled by a microprocessor or computer whose energy is coordinated by said devices with the energy of a fluidic system and where for each pole for each said energy supply, flying leads are connected to inductors which are form fitting to at least one gaussian surface and which holds at least one conically shaped chromatographic LC column or analyte capture column that contains SPE or other functionalized media and at least one filter.

14. The apparatus of claim 1, wherein a manifold of at least one quartz capillary, polymeric or other union is coated on the exterior with a conductor where at least one precision tube of precision length is compression fit into said union where said tubes are fitted to a holder coated with a conductor and connected to the flying leads where said holder contains precision located holes that are of conical or other cross section wherein other tubes or capillaries of different radii can be fit.

15. The apparatus of claim 1, where at least one gaussian surface is made of matter of precision length and radii and where at least one or more of said surfaces are inter connected and coated on the interior and exterior with either polar or non-polar polymers and where each of said gaussian surfaces is of the same or different length and whose exterior is marked with scales and color coded and whose tip, is square cut, beveled or multi-beveled, straight, at an angle, or otherwise cut where said surfaces contain either SPE, chromatographic, or functionalized media, and connected to compressions unions or connector.

16. The apparatus of claim 1, wherein at least one array plate of conductors containing holes in a direction which also has cylindrical tubes in the Y direction of the same pattern, each set independently connected to the HV selector switch and the computer such that energy can be applied to any plate or any tube allowing for the dispensing of a selected position in said array.

17. An inductive method to dispense liquids and their contents in a multiplex manner utilizing the apparatus of claim 1 and an N channel manifold with N channels of said inductors and N channel Gaussian surfaces therein, N channel DC/RF power supplies under computer microprocessor control wherein liquids of biological and other origin are sequentially shot onto, into, or near targets.

18. An inductive method utilizing the apparatus of claim 1 to dispense liquids, slurries, and liquid contents including living matter, using inductively applied and programmed DC or RF or DC/RF energy where after said dispense, dispensed droplets are energized using resistance or IR heaters, prior to introduction to an ESI source in the atmosphere, or prior to and after instrument chambers.

19. A method to dispense liquids, polymers, or other matter utilizing the apparatus of claim 1 where the polarity and the intensity of a HVDC, RF, or HVDC/RF energy is alternated to inductors containing gaussian surfaces connected to pneumatic or other pumps or chips and energized liquids and where such actions and that of a robotic system holding same are computer coordinated to effect accurate dispensing or printing of charged liquids or matter onto non-conductors, conductors and semi-conductors.

* * * * *